US012409150B2

(12) United States Patent
Na et al.

(10) Patent No.: US 12,409,150 B2
(45) Date of Patent: Sep. 9, 2025

(54) pH-SENSITIVE CARBON NANOPARTICLES, PREPARATION METHOD THEREFOR, AND DRUG DELIVERY USING SAME

(71) Applicant: PCE Tech Co., Ltd., Bucheon-si (KR)

(72) Inventors: Kun Na, Bucheon-si (KR); Jeongdeok Seo, Chungcheongnam-do (KR); Dahye Kim, Seoul (KR); Minji Ahn, Seoul (KR)

(73) Assignee: PCE Tech Co., Ltd., Bucheon-si (KR)

( * ) Notice: Subject to any disclaimer, the term of this patent is extended or adjusted under 35 U.S.C. 154(b) by 693 days.

(21) Appl. No.: 17/290,773

(22) PCT Filed: Nov. 5, 2019

(86) PCT No.: PCT/KR2019/014888
§ 371 (c)(1),
(2) Date: May 2, 2021

(87) PCT Pub. No.: WO2020/096318
PCT Pub. Date: May 14, 2020

(65) Prior Publication Data
US 2021/0369634 A1  Dec. 2, 2021

(30) Foreign Application Priority Data

Nov. 5, 2018  (KR) .................. 10-2018-0134565
Nov. 4, 2019  (KR) .................. 10-2019-0139463

(51) Int. Cl.
*A61K 9/51*  (2006.01)
*A61K 45/06*  (2006.01)

(52) U.S. Cl.
CPC ............ *A61K 9/5192* (2013.01); *A61K 45/06* (2013.01)

(58) Field of Classification Search
CPC .............................. A61K 9/5192; A61K 45/06
See application file for complete search history.

(56) References Cited

FOREIGN PATENT DOCUMENTS

KR  10-2008-0006847 A     1/2008
WO  WO-2013191965 A1 * 12/2013 ........... A61K 31/519

OTHER PUBLICATIONS

Lei et al. PH-sensitive nanoparticles of derivated dextran grafted with 1-(3-aminopropyl) imidazole, Advanced Materials Research Online: Jul. 9, 2012 ISSN: 1662-8985, vol. 549, pp. 131-136 (Year: 2012).*
Shah et al. Comparison of Conventional and Microwave-assisted Synthesis of Benzotriazole Derivatives,Indian Journal of Pharmaceutical Sciences Jan.-Feb. 2014, pp. 46-53. (Year: 2014).*
Li Ruiyi et al. Histidine-functionalized carbon-based dot-Zinc(II) nanoparticles as a novel stabilizer for Pickering emulsion synthesis of polystyrene microspheres, Journal of Colloid and Interface Science 493 (2017) 24-31 (Year: 2017).*
https://www.sigmaaldrich.com/US/en/search/histidine?control=force_type_false&focus=products&page=1&perpage=30&sort=relevance&term=histidine&type=product (accessed Oct. 2023) (Year: 2023).*
https://www.vanderbilt.edu/AnS/Chemistry/Rizzo/stuff/AA/AminoAcids.html (accessed Oct. 2023) (Year: 2023).*
https://cwsimons.com/how-to-determine-the-net-charge-of-amino-acids/ (accessed Oct. 2023) (Year: 2023).*
Shah et al. Comparison of Conventional and Microwave-assisted Synthesis of Benzotriazole Derivatives, Indian Journal of Pharmaceutical Sciences Jan.-Feb. 2014, pp. 46-53. (Year: 2014) (Year: 2014).*
Zeng et al. Carbon dots as a trackable drug delivery carrier for localized cancer therapy in vivo†, J. Mater. Chem. B, 2016, 4, 5119 (Year: 2016).*
Ruiyi et al. Histidine-functionalized carbon-based dot-Zinc(II) nanoparticles as a novel stabilizer for Pickering emulsion synthesis of polystyrene microspheres, Journal of Colloid and Interface Science 493 (2017) 24-31 (Year: 2017).*
Delavari et al. A biophysical study on the mechanism of interactions of DOX or PTX with a-lactalbumin as a delivery carrier, www.nature.com/scientificreports, Nov. 26, 2018 (Year: 2018).*
Ontrol=force_type_false&focus=products&page=1&perpage=30&sort=relevance&term=histidine&type=product (accessed Oct. 2023) (Year: 2023) (Year: 2023).*
Yang et al. Conventional and Microwave Hydrothermal Synthesis and Application of Functional Materials: A Review, Published: Apr. 11, 2019, Materials (Year: 2019).*
https://pubchem.ncbi.nlm.nih.gov/compound/Lomustine (accessed Oct. 2024) (Year: 2024).*
International Search Report for PCT/KR2019/014888 mailed Feb. 20, 2020 from Korean Intellectual Property Office.
Ruiyi, Li et al., "Histidine-functionalized carbon-based dot-Zinc(II) nanoparticles as a novel stabilizer for Pickering emulsion synthesis of polystyrene microspheres", Journal of Colloid and Interface Science, 2017, vol. 493, pp. 24-31.
Lei, He et al., "PH-sensitive nanoparticles of derivated dextran grafted with 1-(3-aminopropyl) imidazole", Advanced Materials Research, 2012, vol. 549, pp. 131-136.
Zeng, Qinghui et al., "Carbon dots as a trackable drug delivery carrier for localized cancer therapy in vivo", Journal of Materials Chemistry B, 2016, vol. 4, pp. 5119-5126.
Wang, Xudong et al., "Imidazole derivative-functionalized carbon dots: Using as a fluorescent probe for detecting water and imaging of live cells", Dalton Transactions, 2015, vol. 44, No. 12, pp. 5547-5554.

(Continued)

*Primary Examiner* — Robert A Wax
*Assistant Examiner* — John W Lippert, III
(74) *Attorney, Agent, or Firm* — Revolution IP, PLLC

(57) ABSTRACT

The present invention relates to pH-sensitive carbon nanoparticles, a method of preparing the same, and a drug delivery using the same, and pH-sensitive carbon nanoparticles including imidazole is prepared so that a hydrophobic drug and a photosensitizer material can be encapsulated, drug release is possible under weakly acidic conditions, and thus it can be used as a drug carrier for anticancer treatment, photodynamic therapy, or photomediated anticancer immunotherapy.

9 Claims, 26 Drawing Sheets

(56) References Cited

OTHER PUBLICATIONS

Wooram Park et al., "Intermolecular Structural Change for Thermoswitchable Polymeric Photosensitizer", J Am Chem Soc. Aug. 3, 20161; 138(34): 10734-10737.
Eun Seong Lee et al., "Tumor pH-responsive flower-like micelles of poly(L-lactic acid)-b-poly(ethylene glycol)-b-poly(L-histidine)", J Control Release. Oct. 18, 2007; 123(1): 19-26.

* cited by examiner

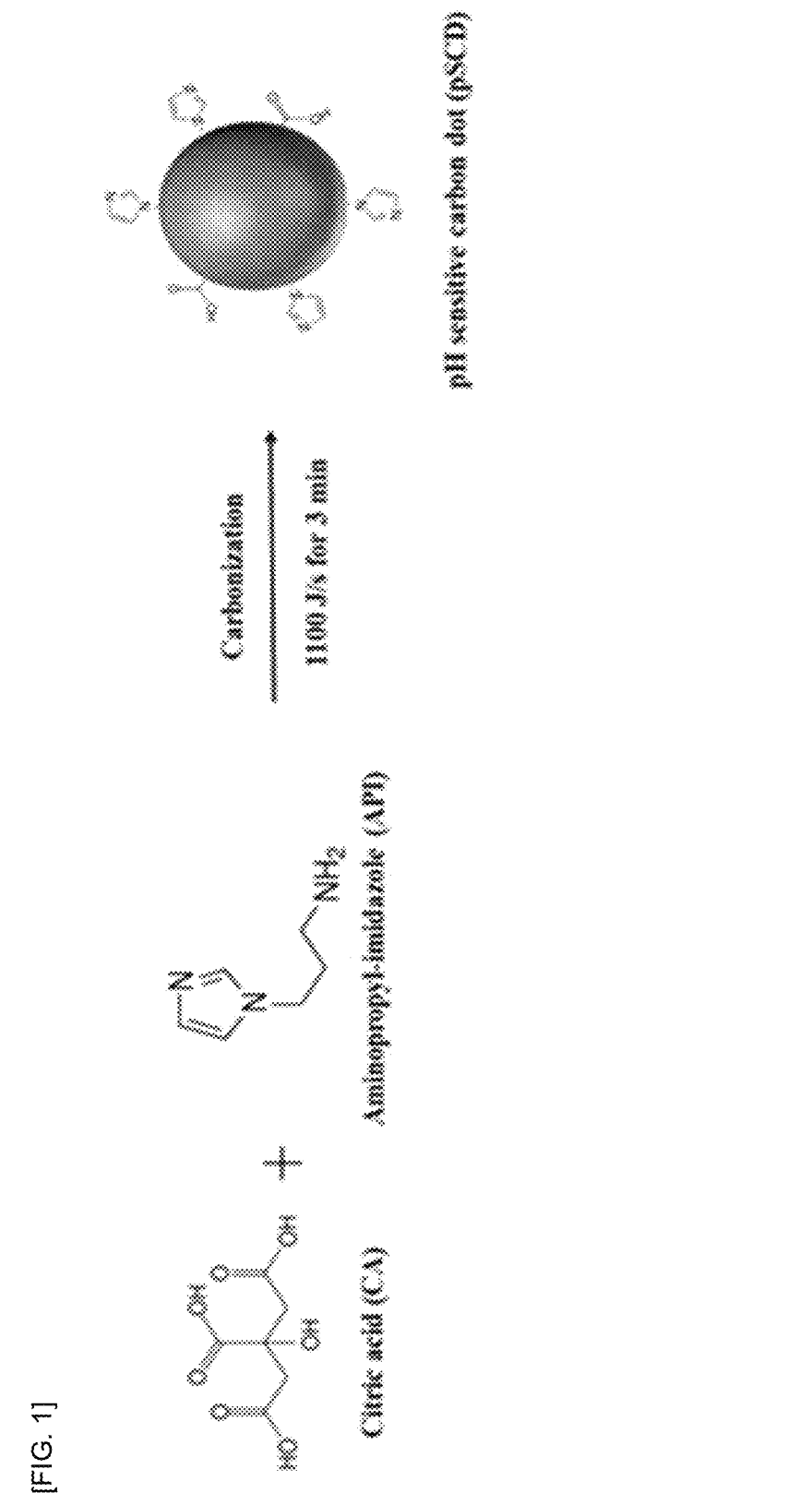
[FIG. 1]

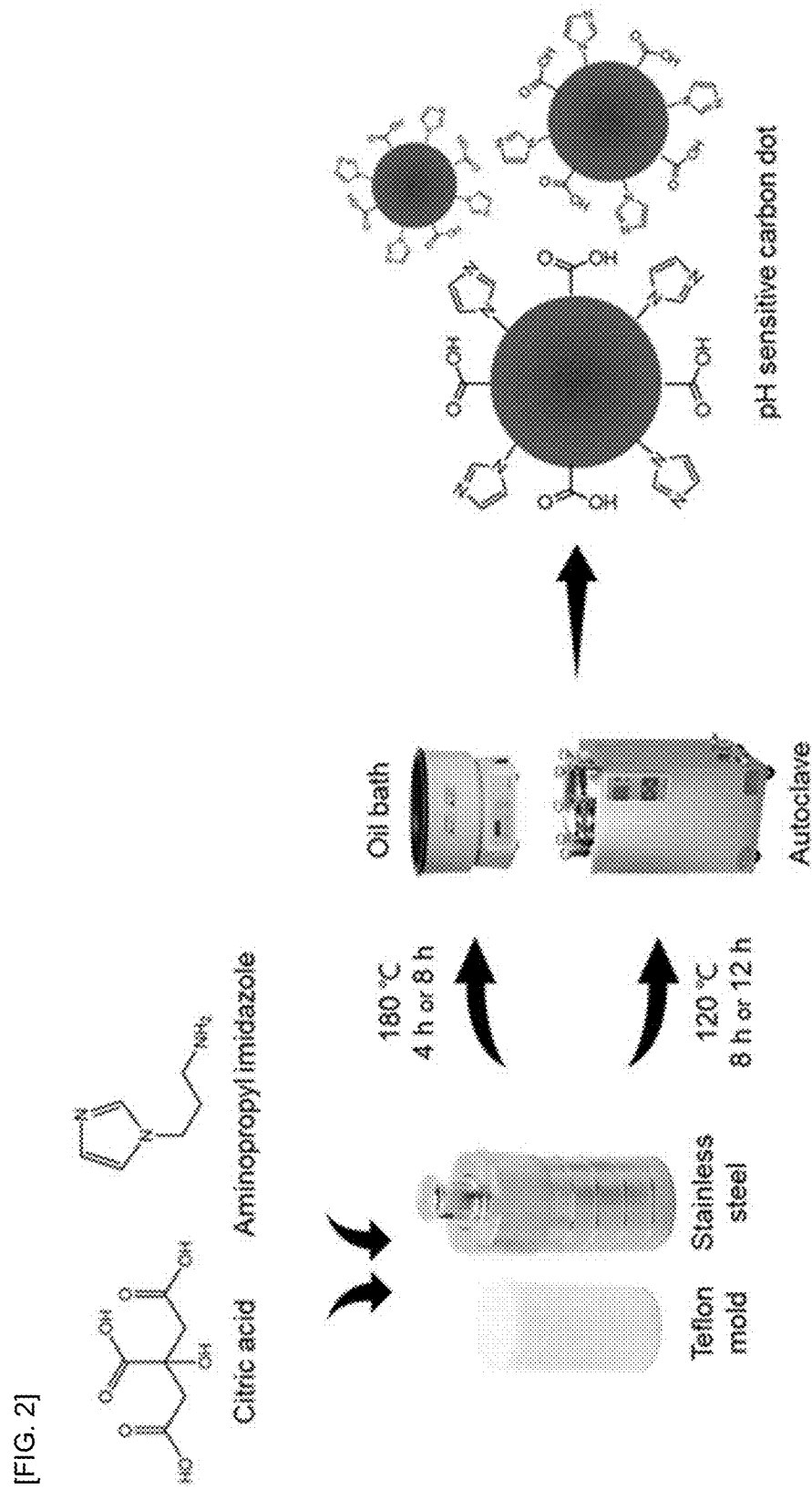
[FIG. 2]

[FIG. 3]
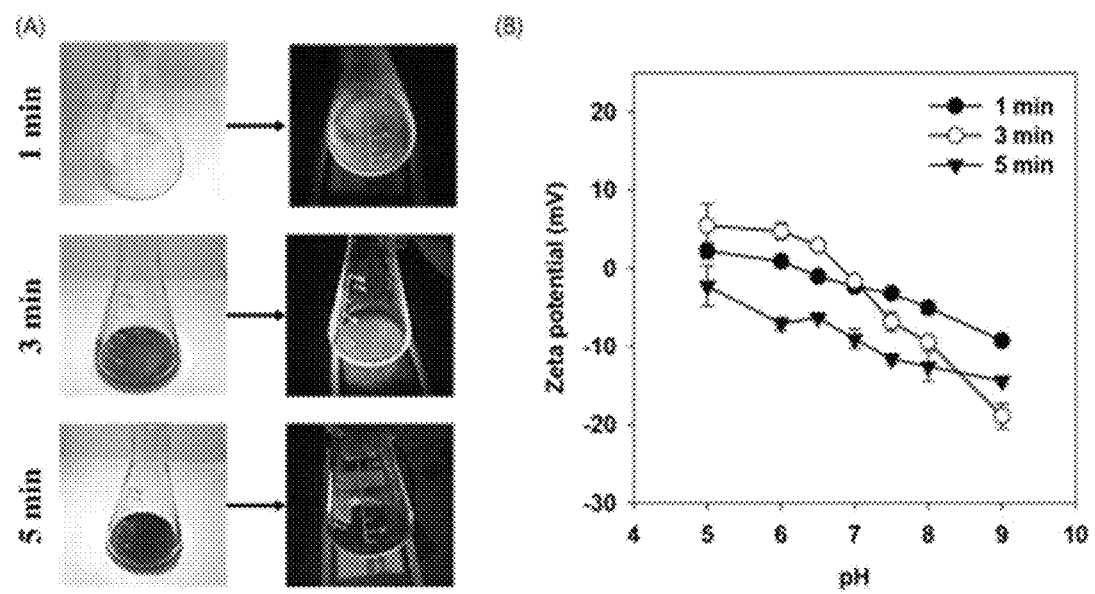

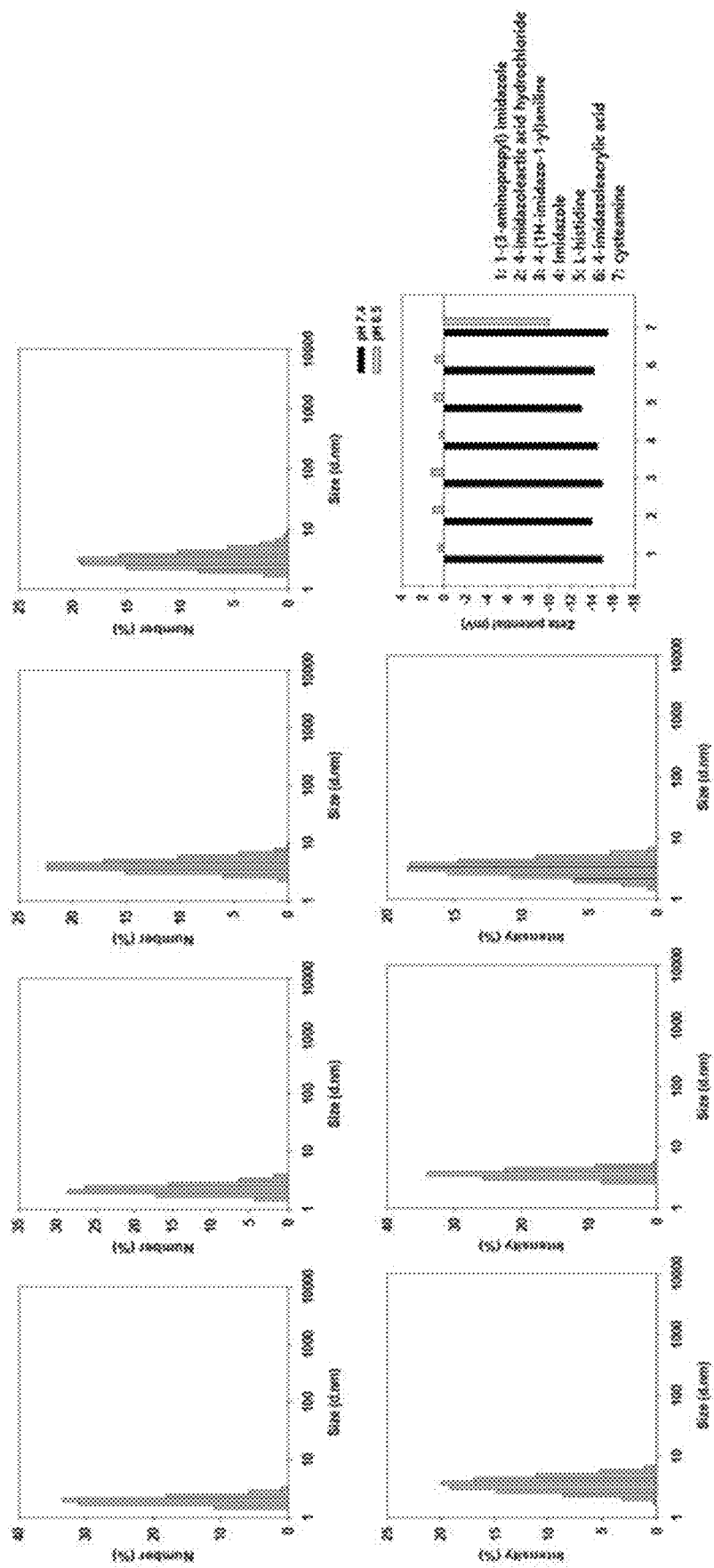
[FIG. 4]

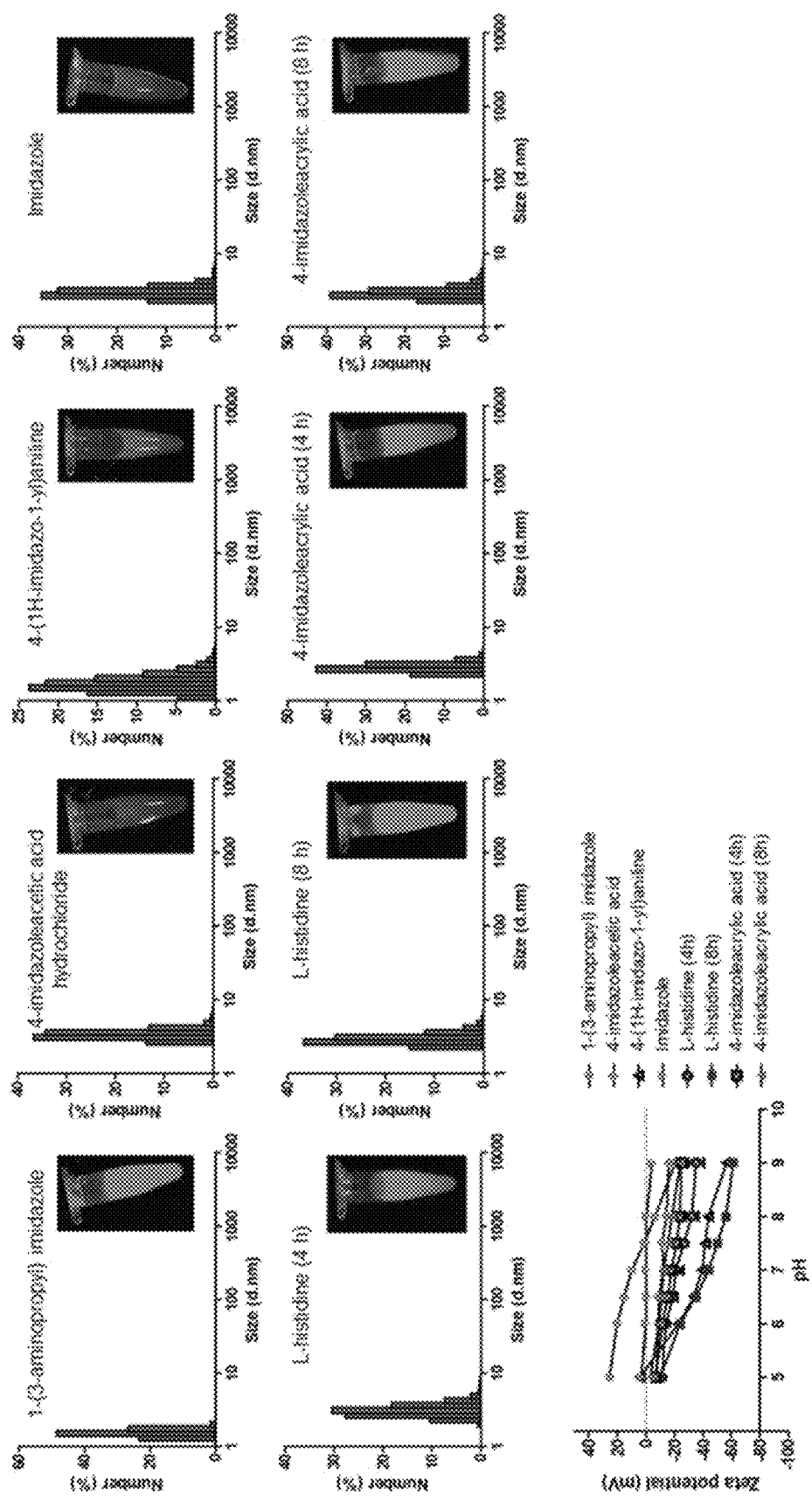
[FIG. 5]

[FIG. 6]
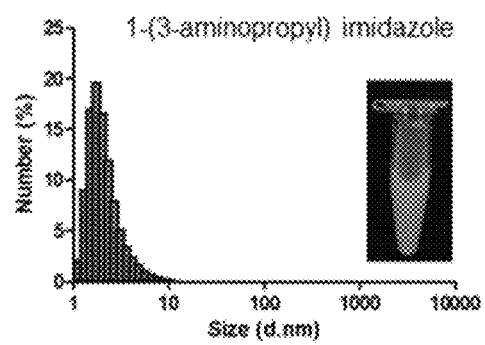
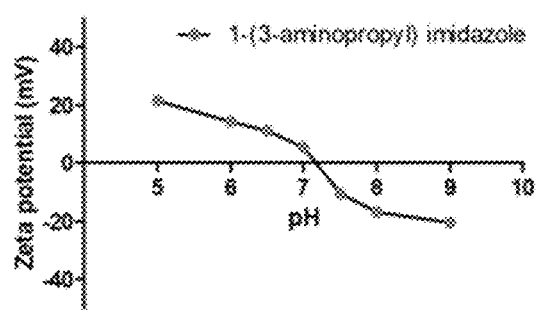

[FIG. 7]
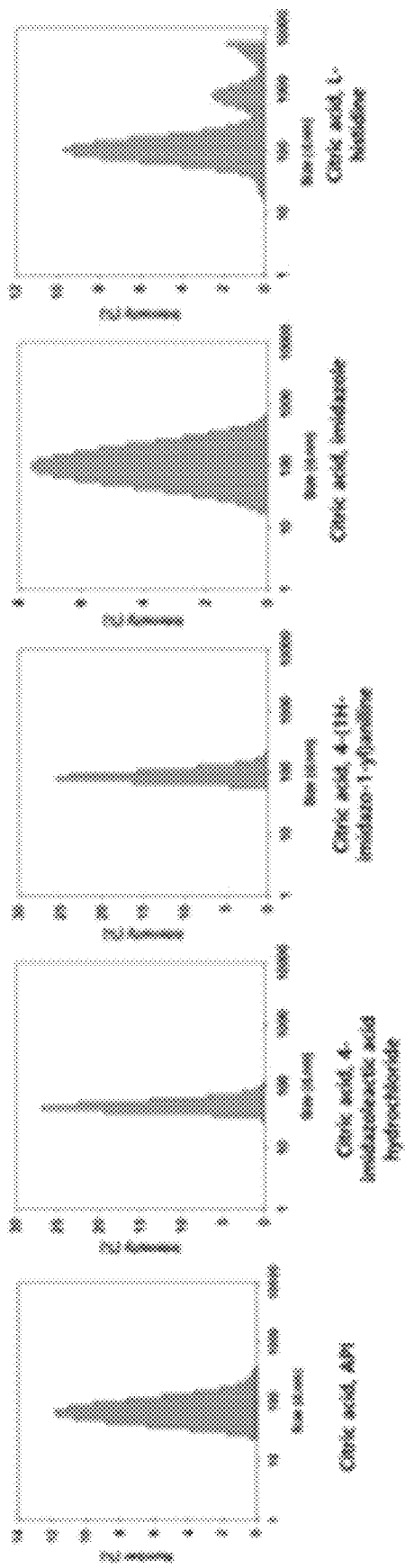
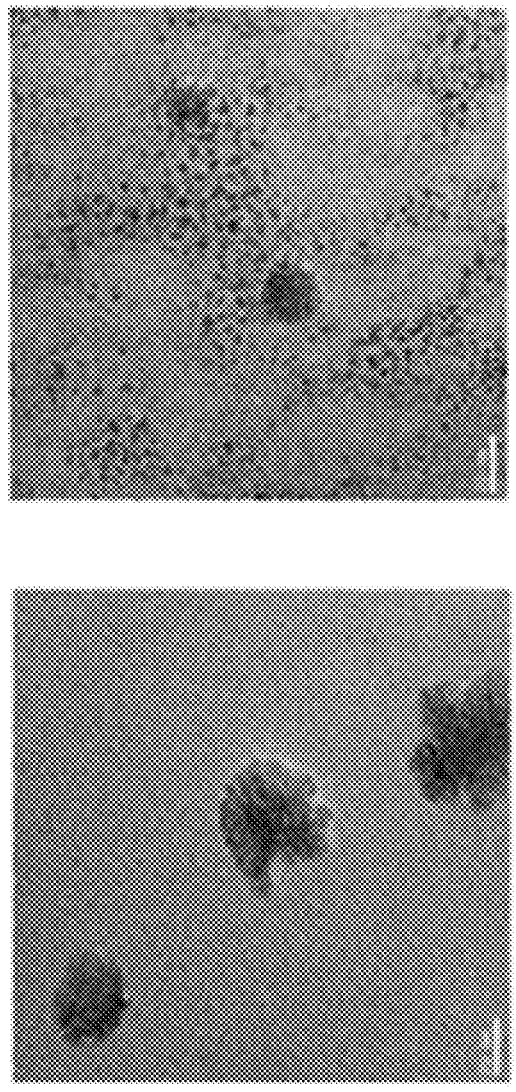

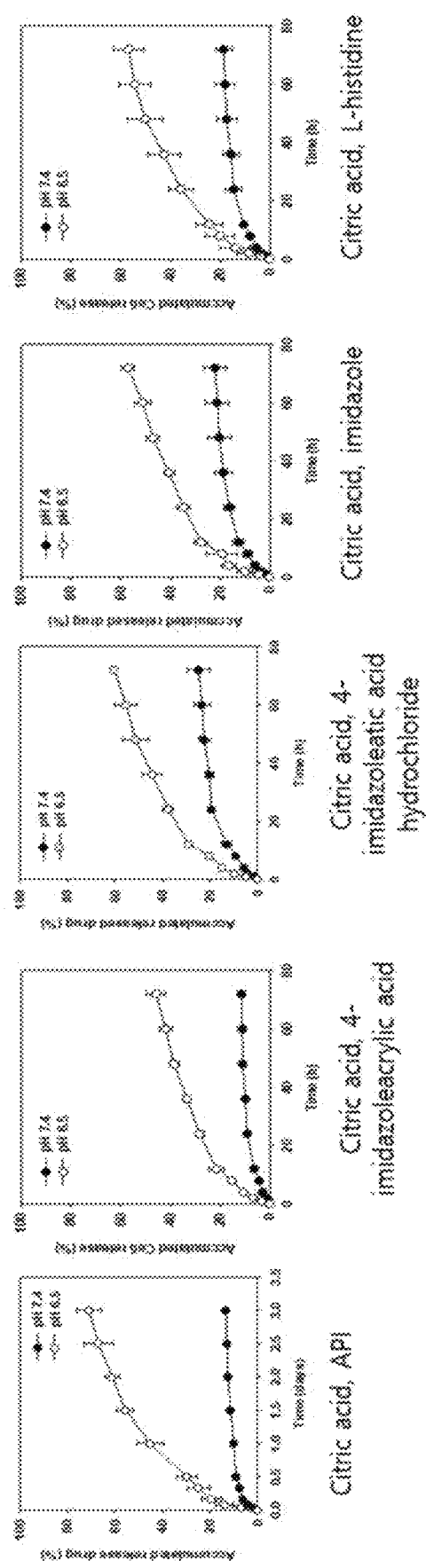
[FIG. 8]

[FIG. 9]
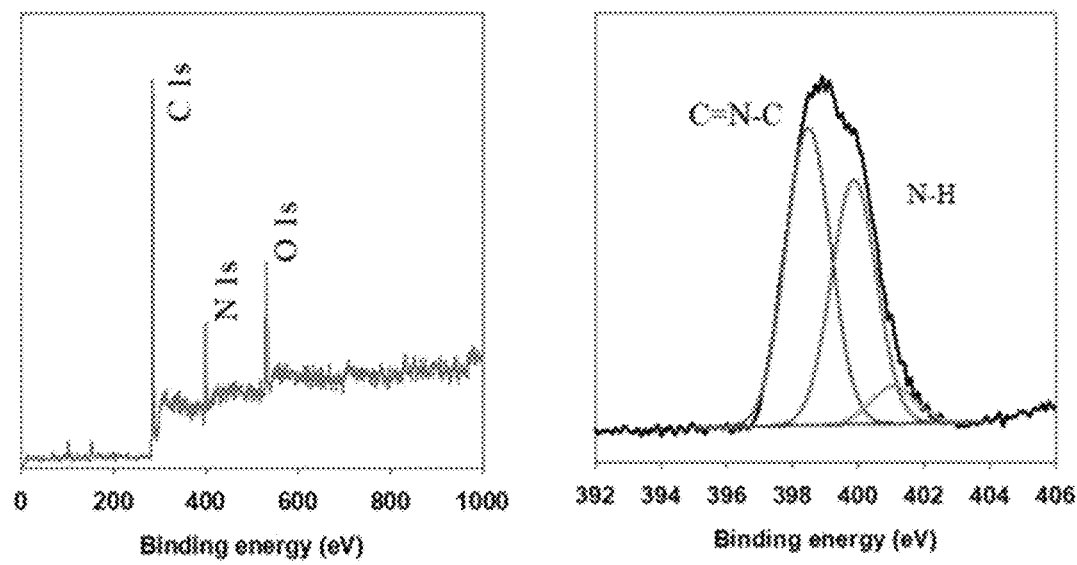
[FIG. 10]
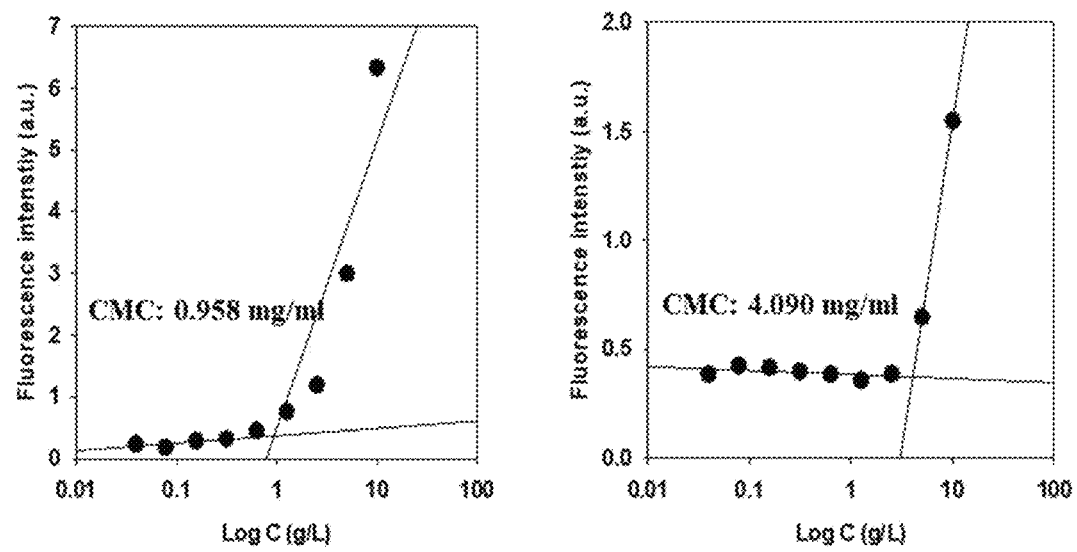

[FIG. 11]
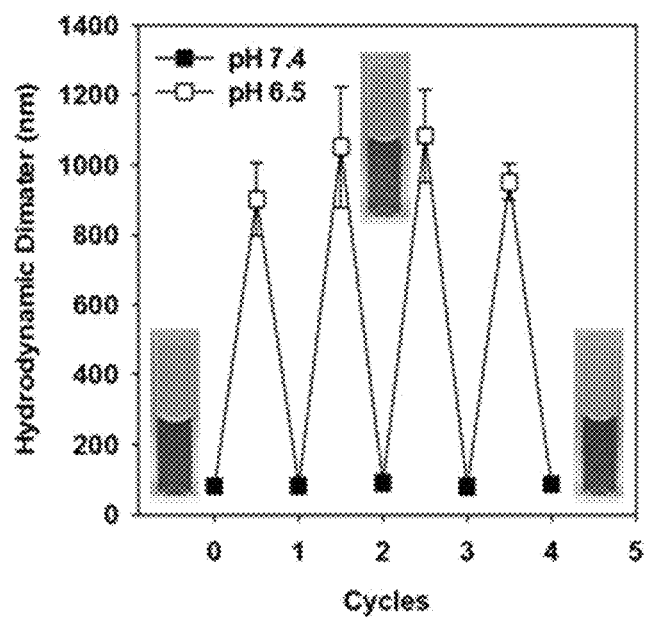
[FIG. 12]
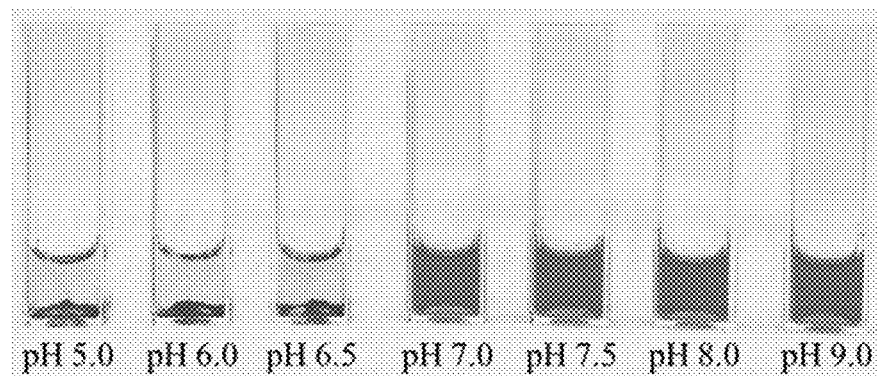

[FIG. 13]
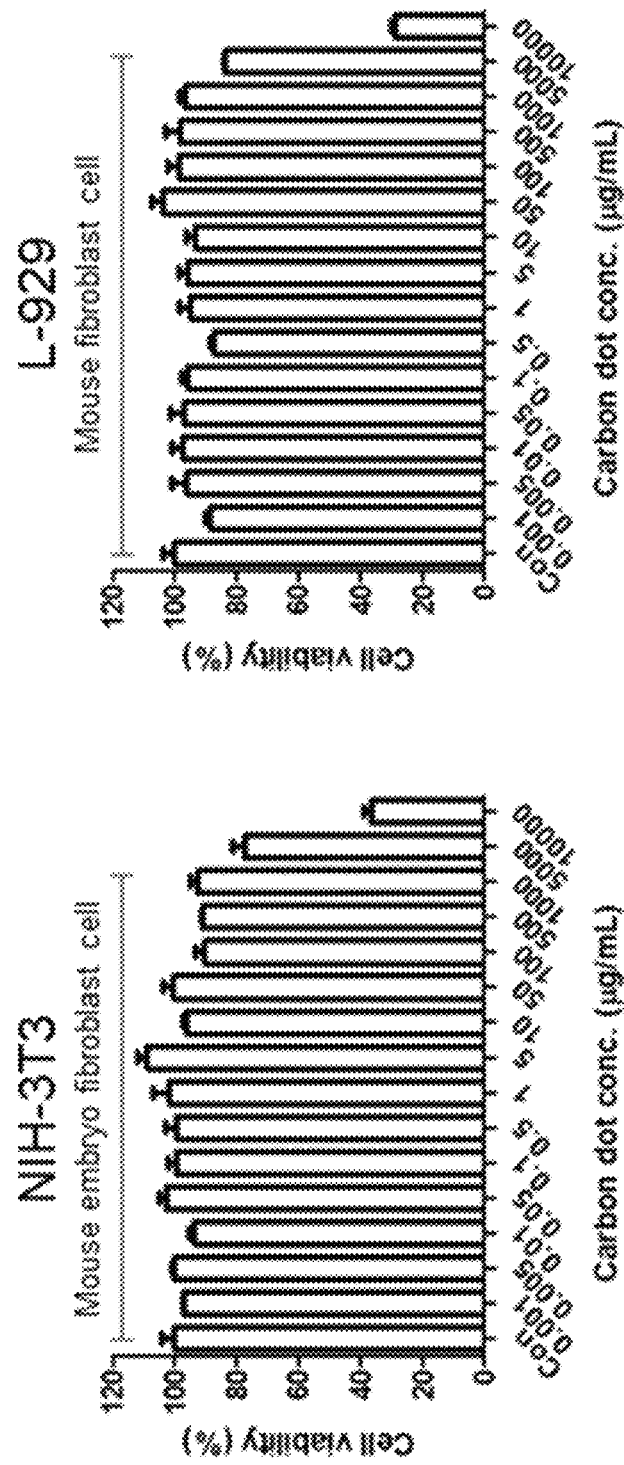

[FIG. 14]
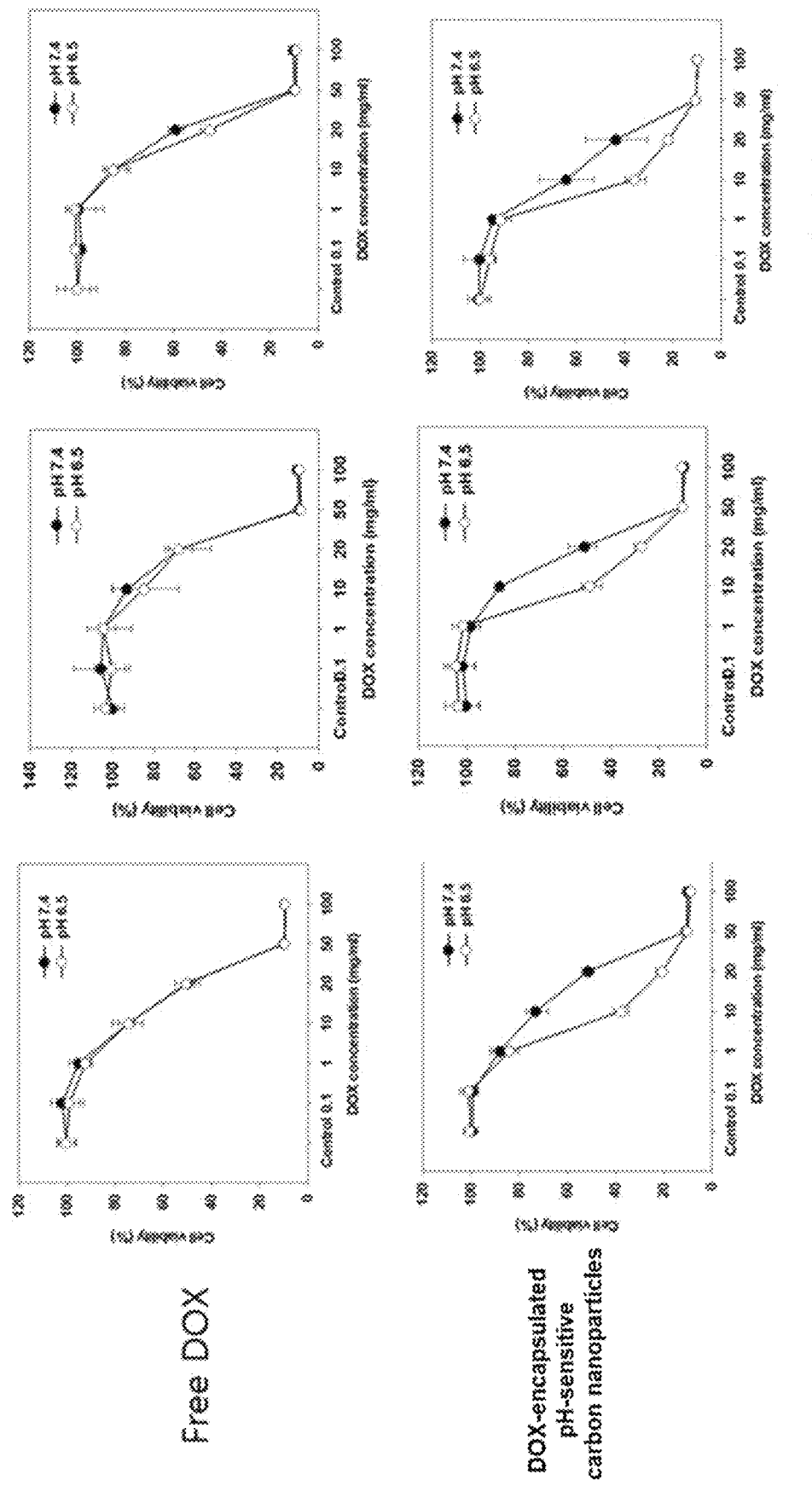

[FIG. 15]
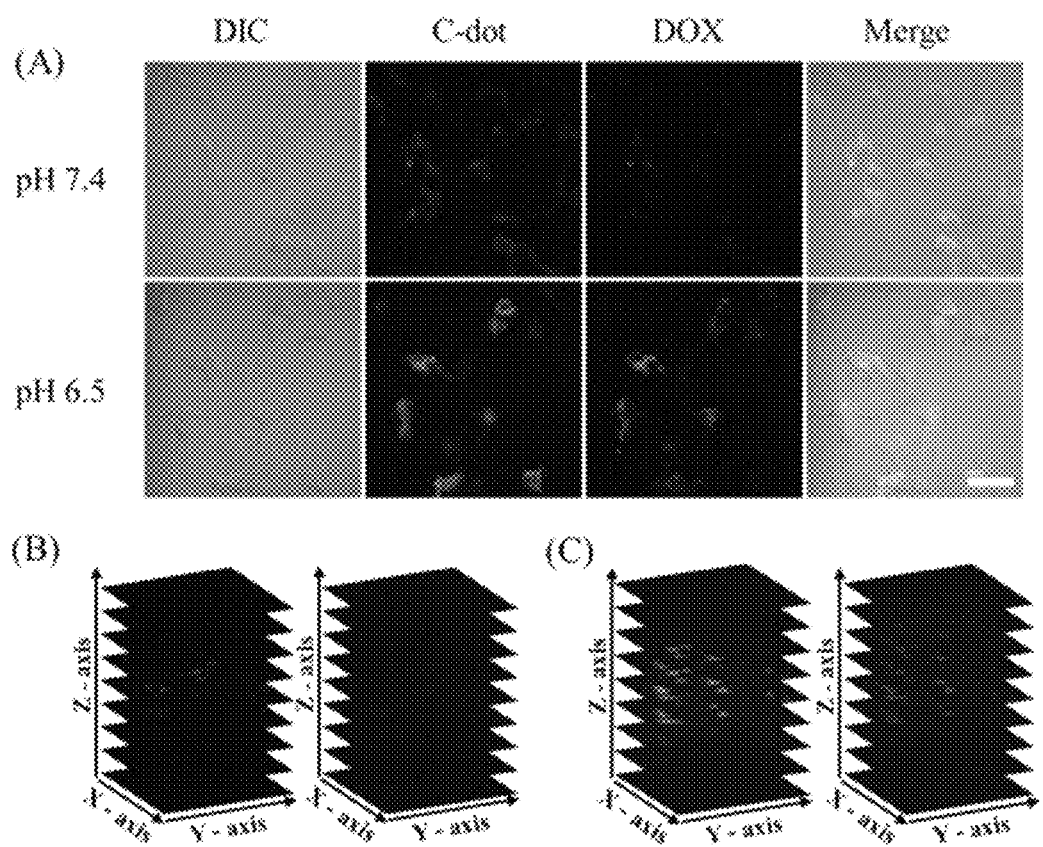

[FIG. 16]
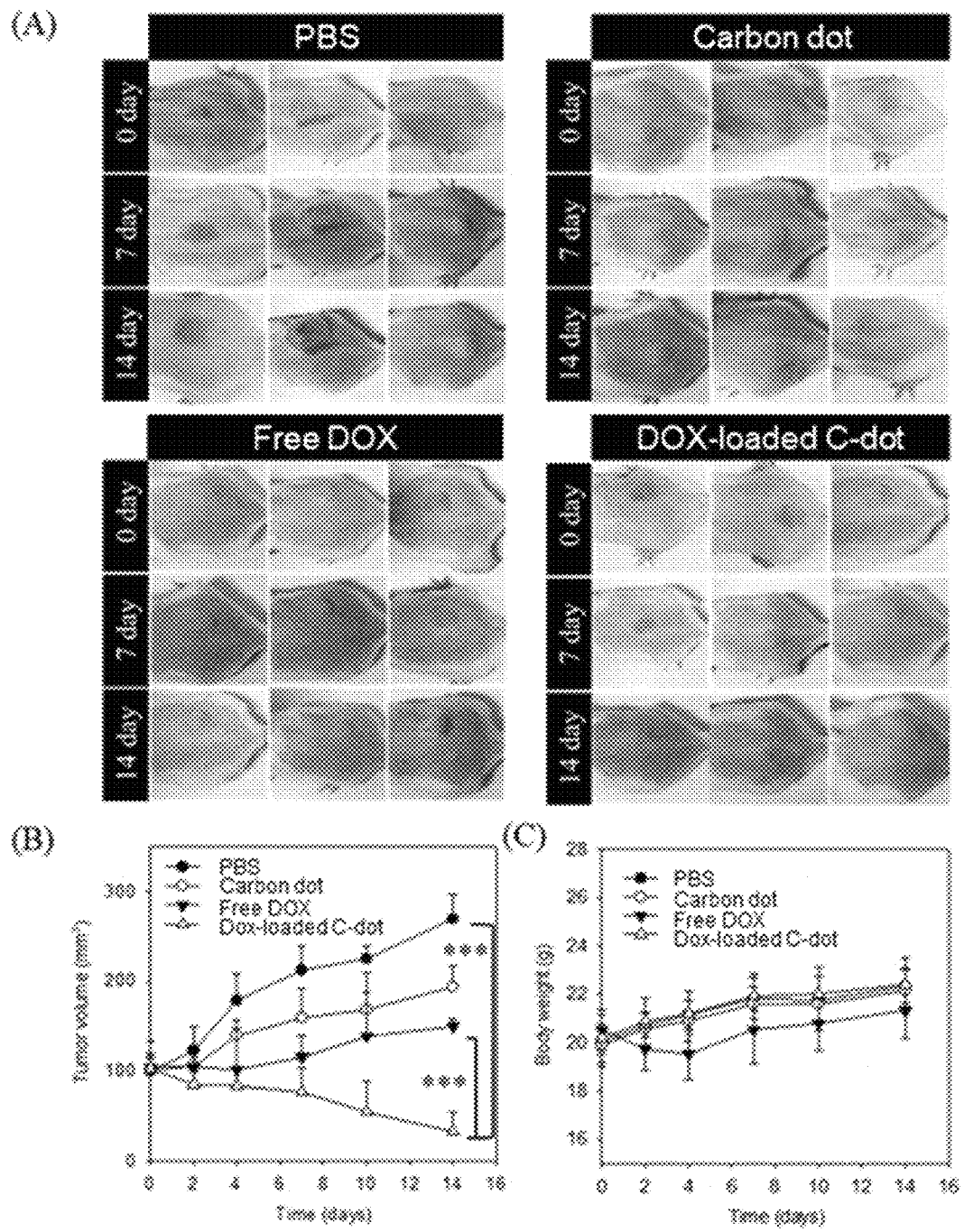

[FIG. 17]
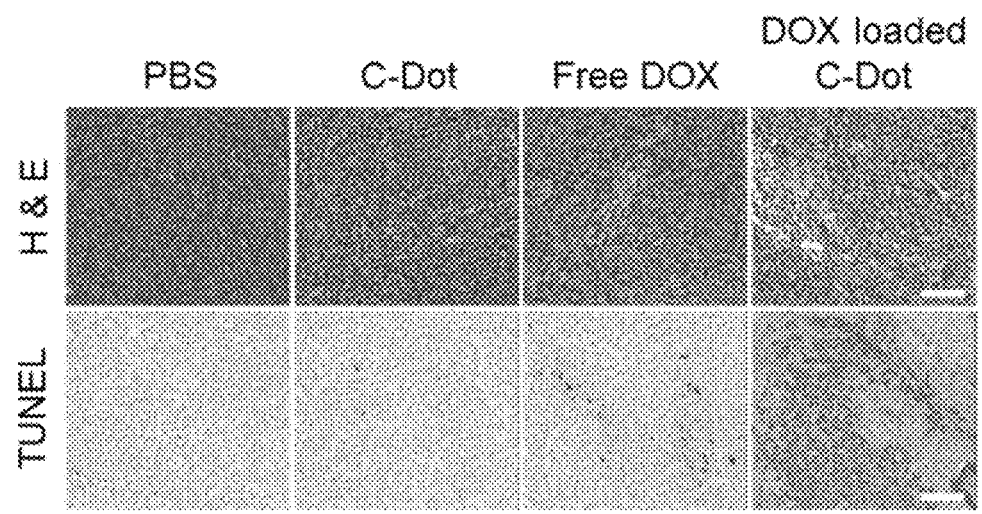

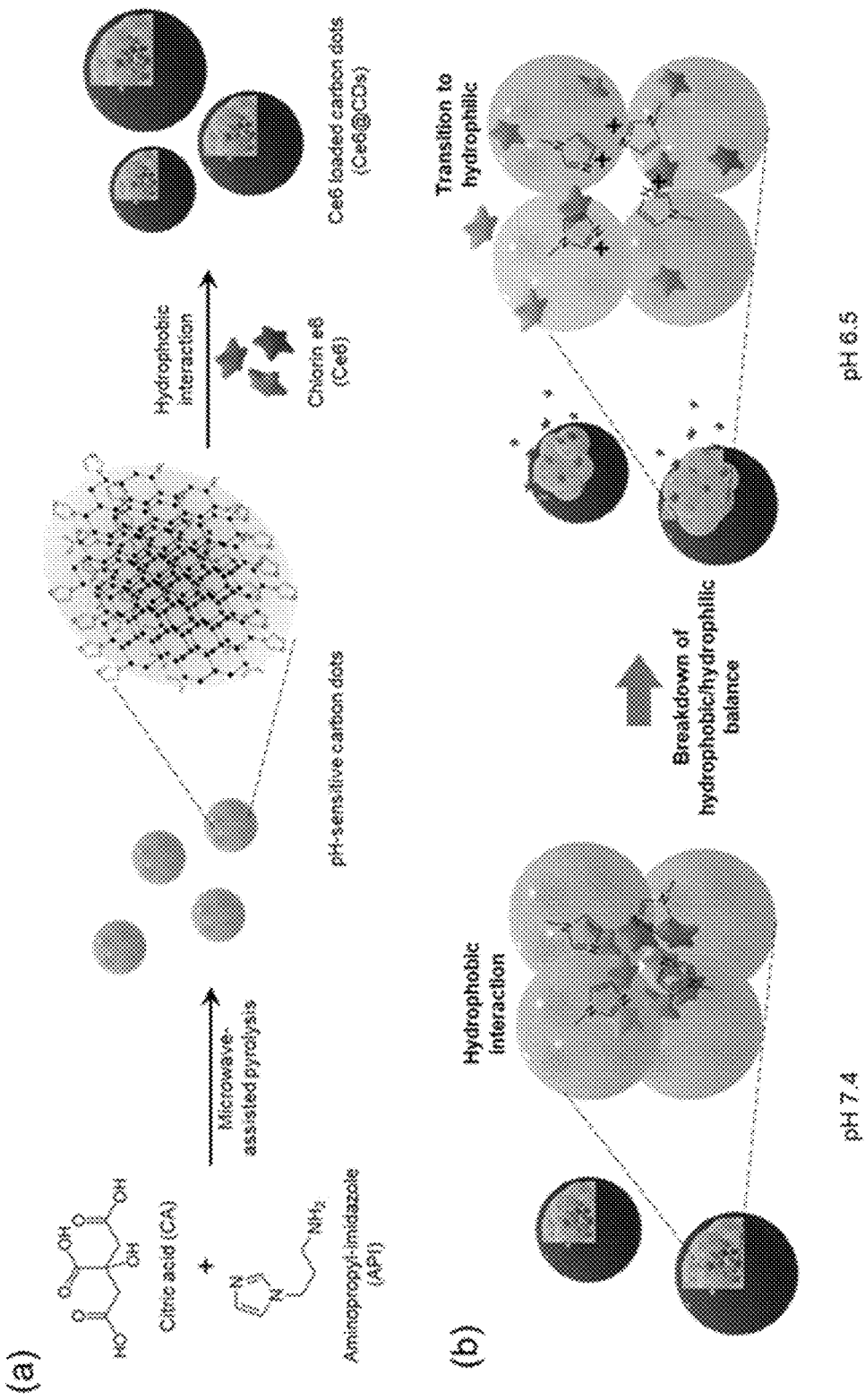
[FIG. 18]

[FIG. 19]
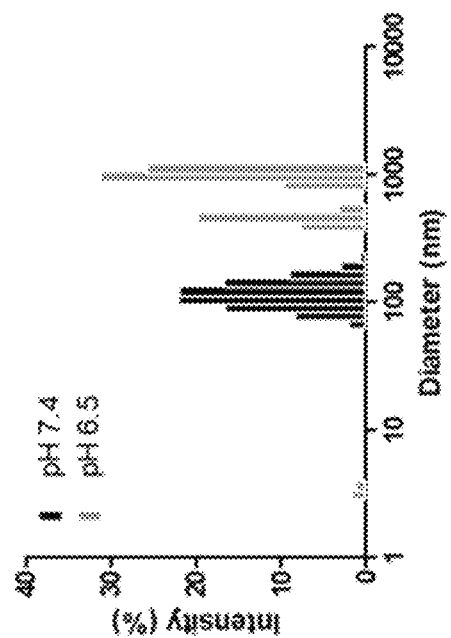
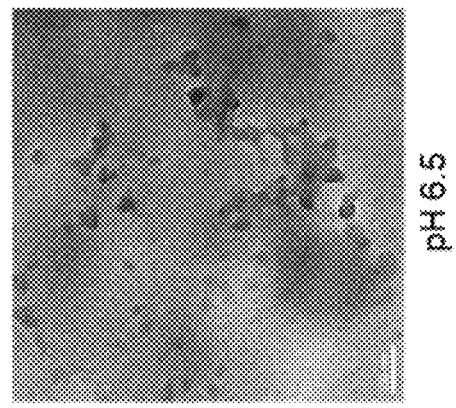
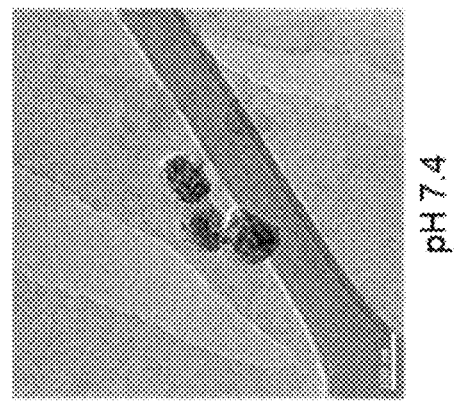

[FIG. 20]
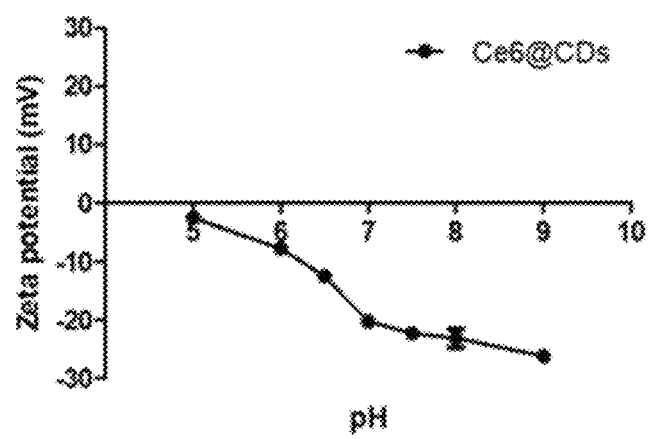

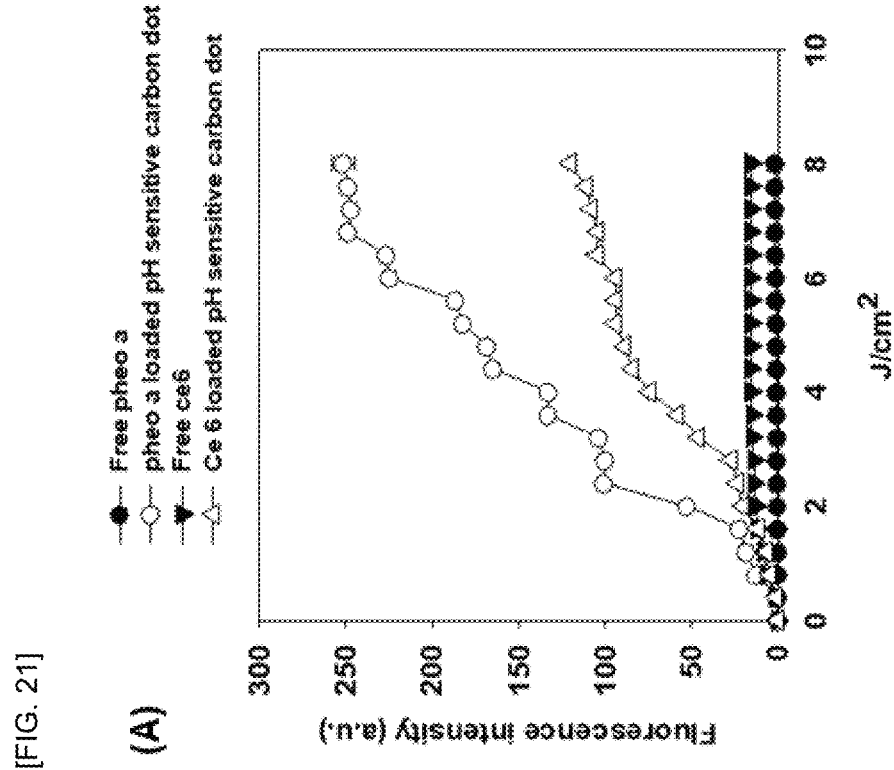
[FIG. 21]

[FIG. 22]
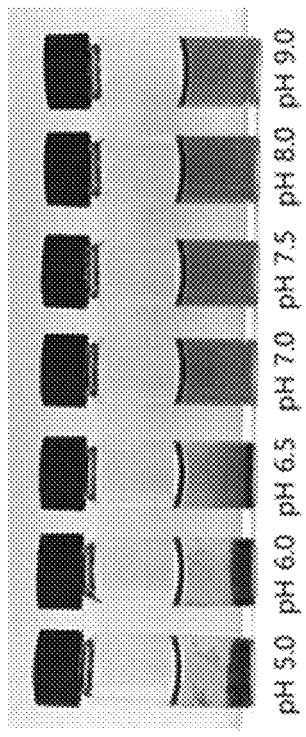
[FIG. 23]
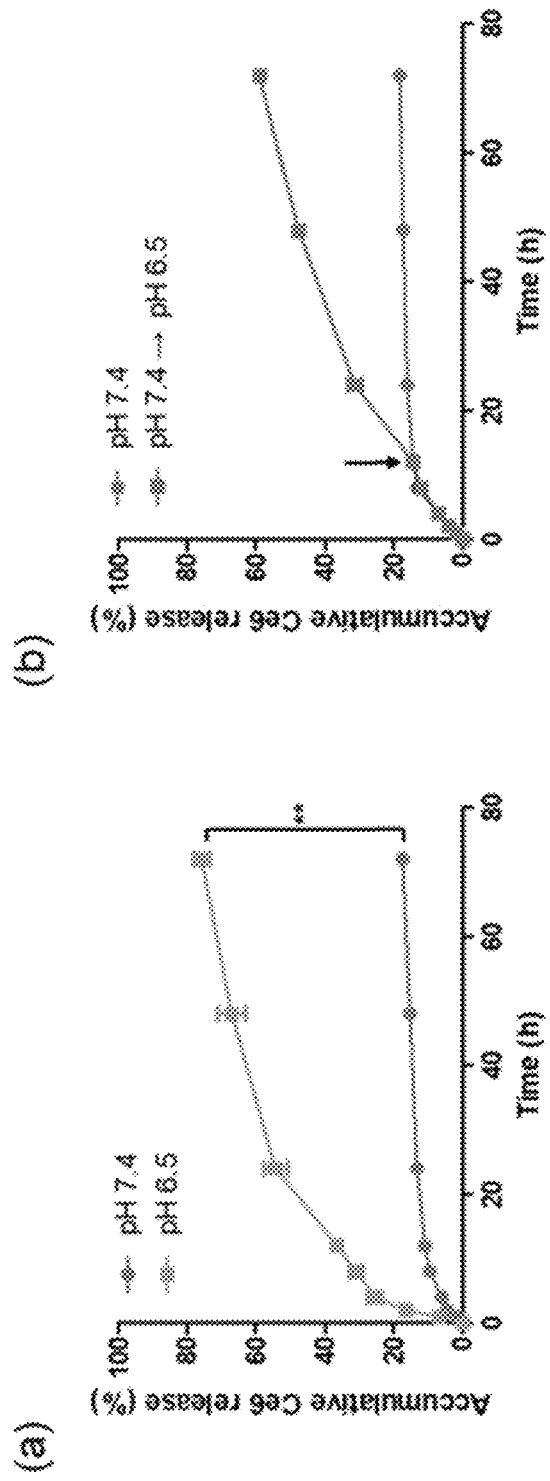

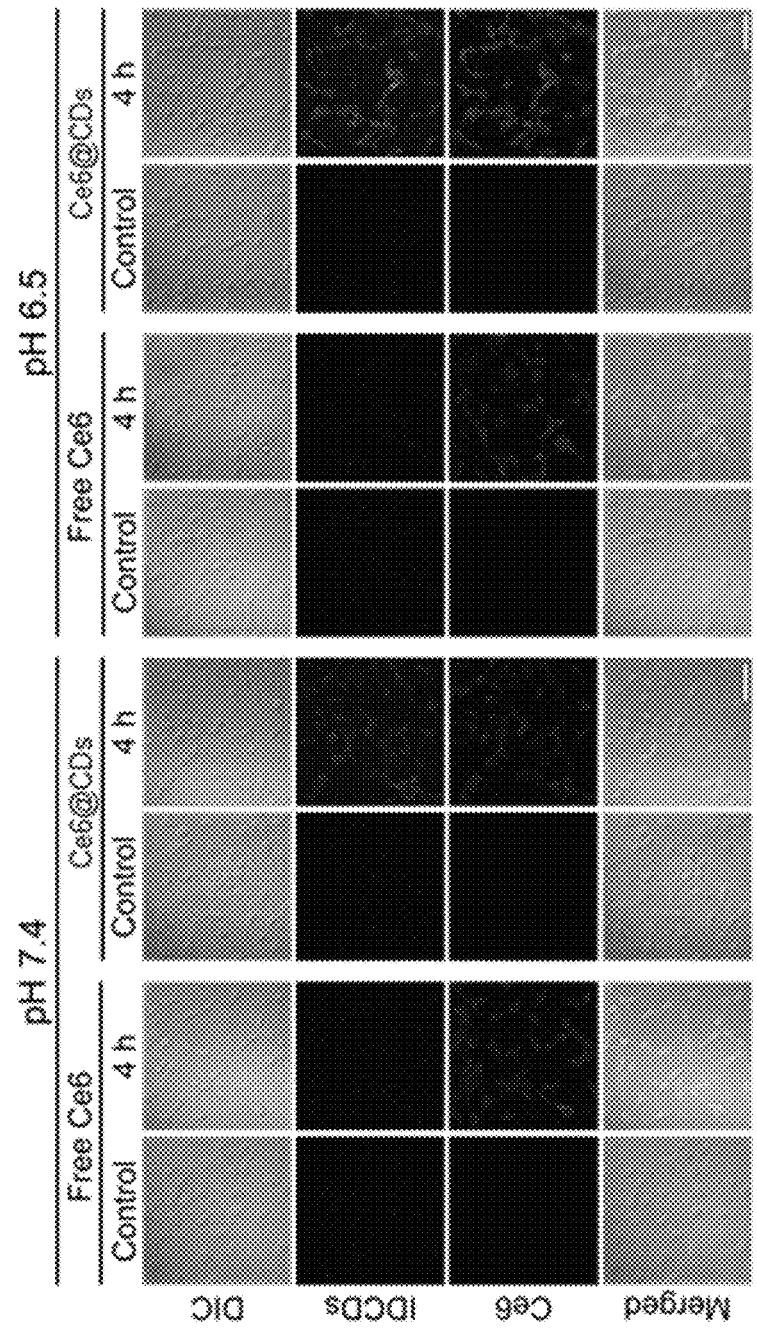
[FIG. 24]

[FIG. 25]
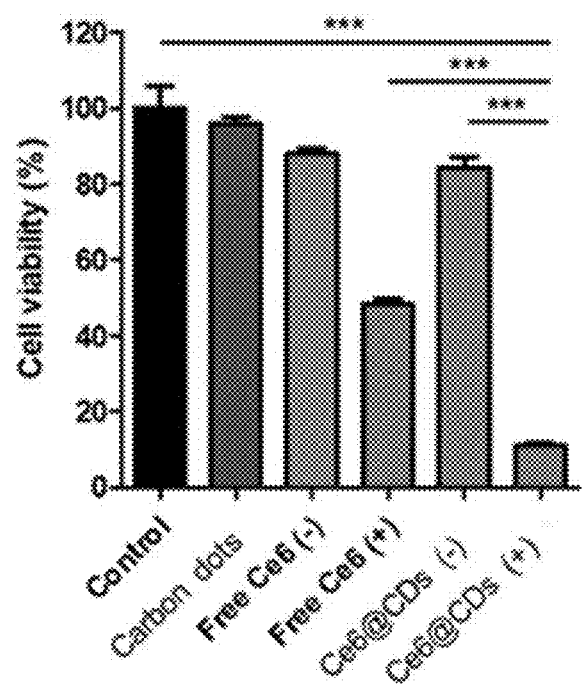

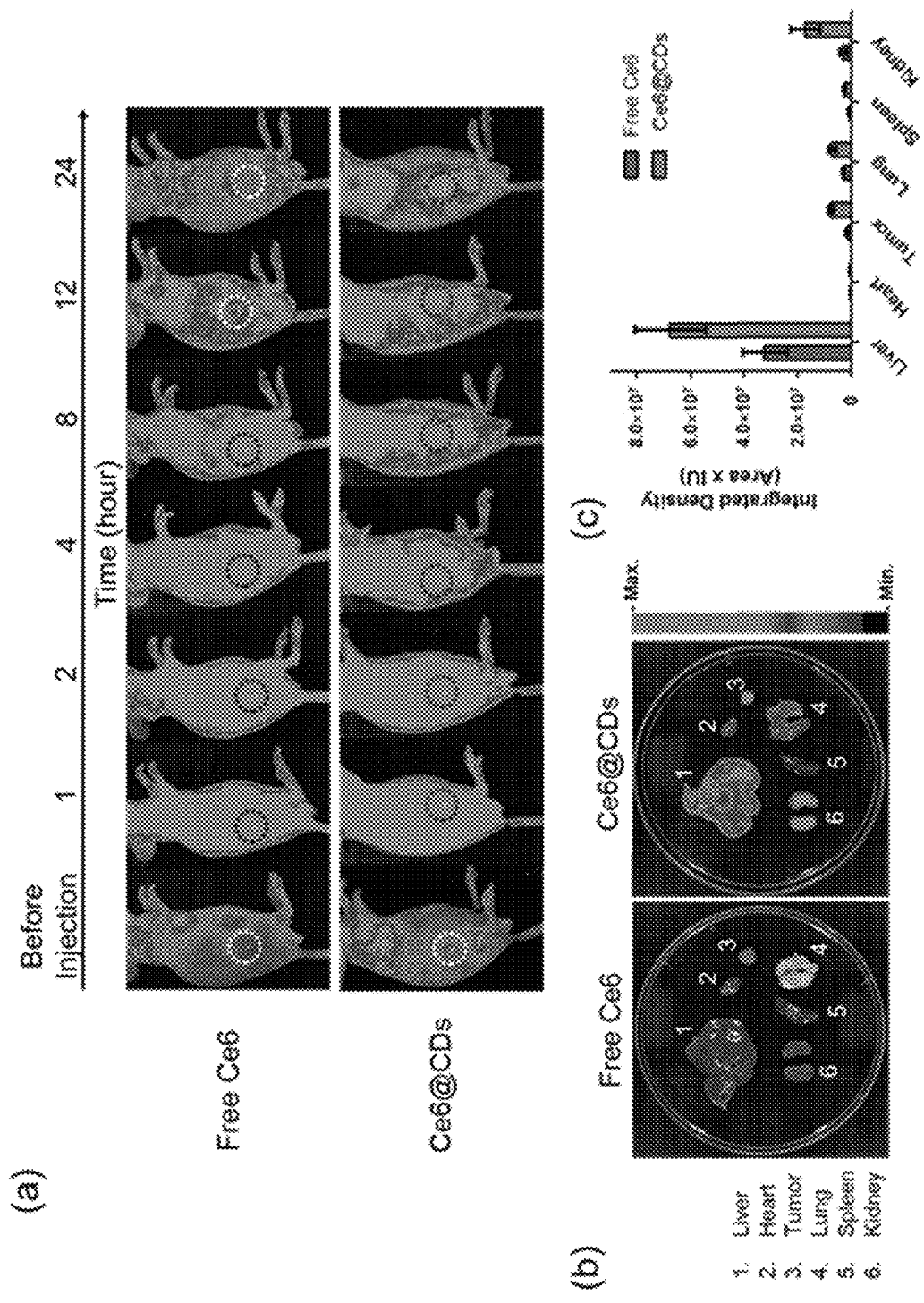
[FIG. 26]

[FIG. 27]
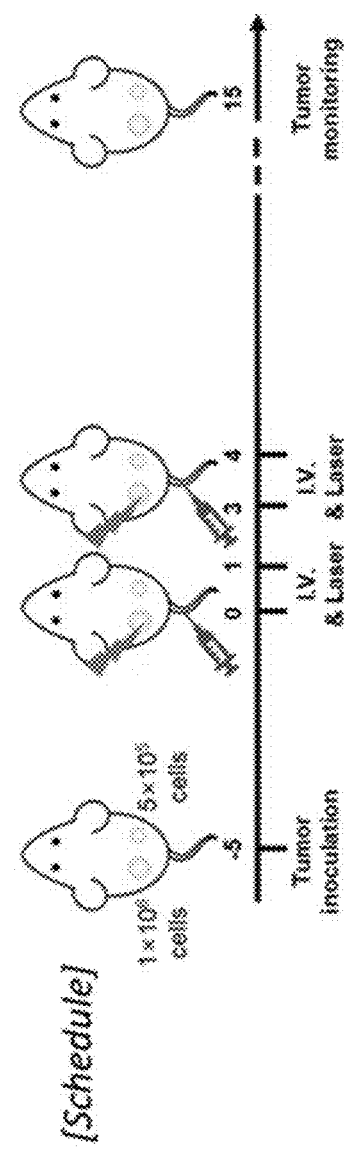
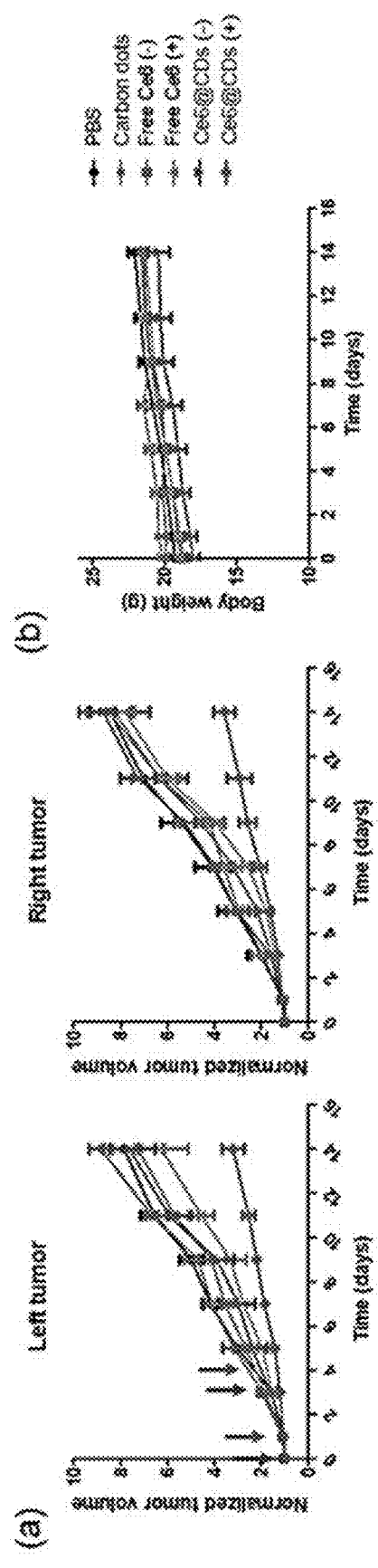

[FIG. 28]
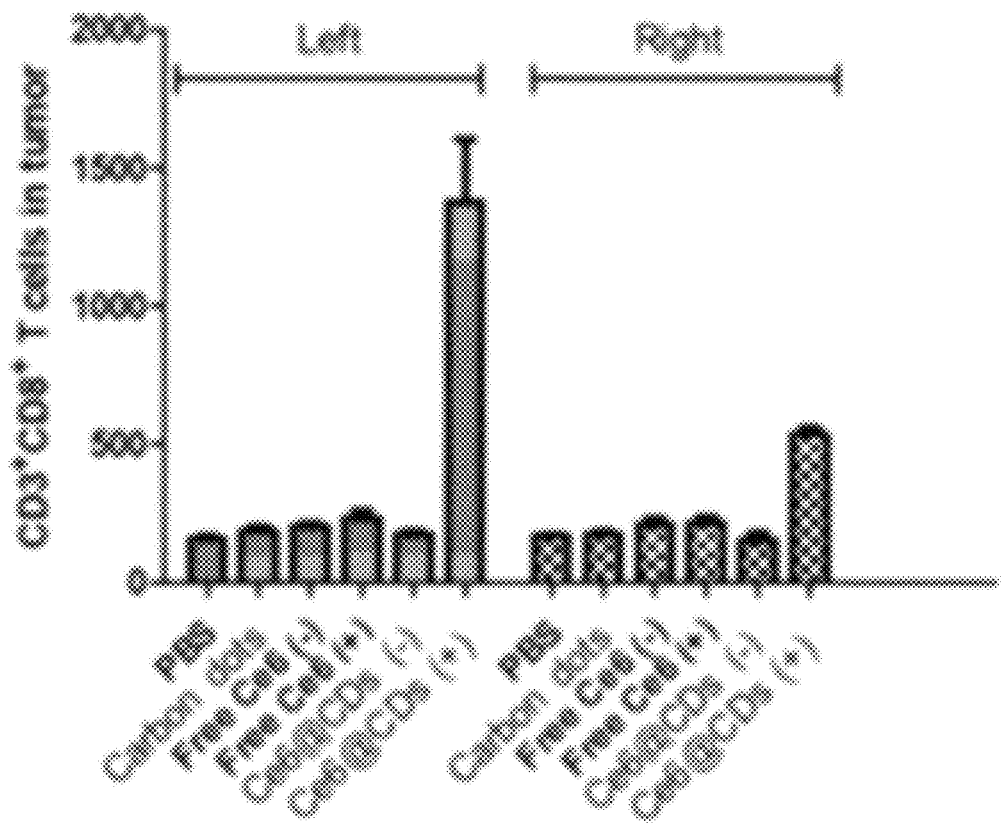
[FIG. 29]
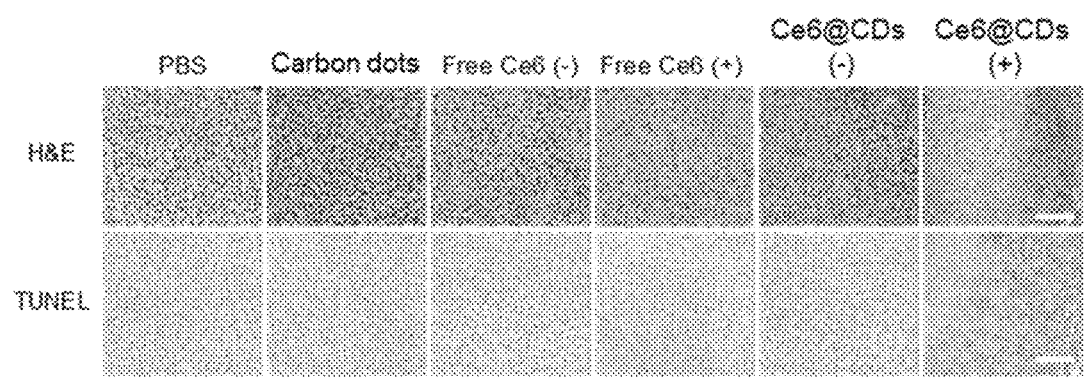

[FIG. 30]
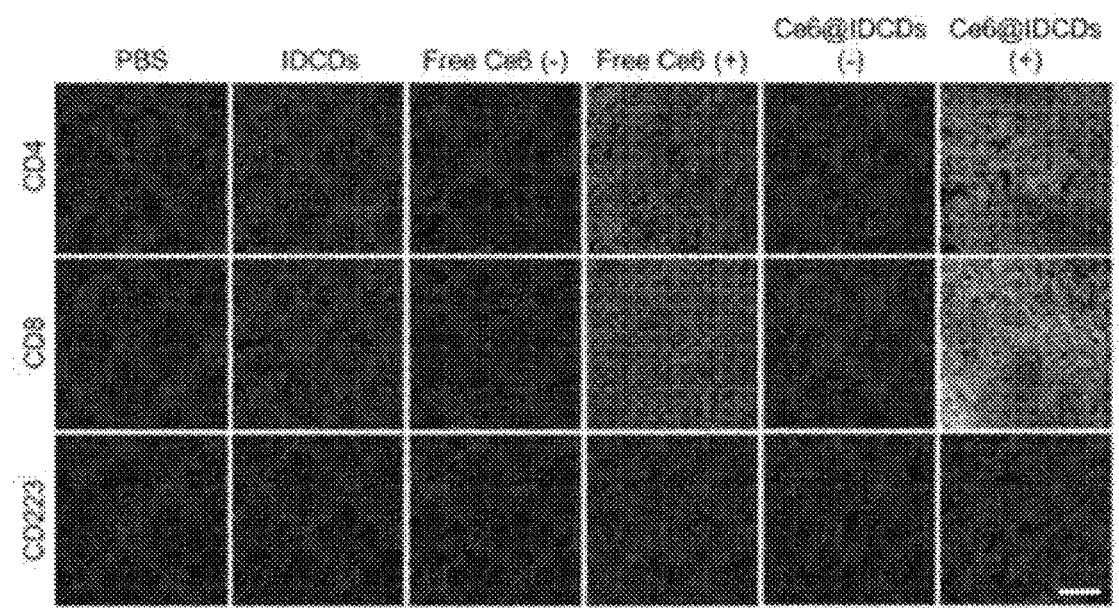

ପH-SENSITIVE CARBON NANOPARTICLES, PREPARATION METHOD THEREFOR, AND DRUG DELIVERY USING SAME

TECHNICAL FIELD

The present invention relates to a pH-sensitive carbon nanoparticle, a method of preparing the same, and drug delivery using the same.

BACKGROUND ART

Drug carriers using polymers have been mainly studied for the delivery of anticancer drugs, and induce an increase in the in vivo residence time and targeting rate of anticancer drugs, thereby reducing side effects of anticancer drugs and increasing anticancer effects. However, it was difficult to expect the desired effect because the release of the encapsulated anticancer agent could not be controlled. Accordingly, research on drug carriers that are sensitive to various stimuli (light, pH, magnetic field, temperature, enzymes, etc.) is actively conducted. These are in the spotlight because they remain stable in normal tissues, but when they reach the cancer site, drugs are released by stimulation, which can significantly reduce side effects and increase anticancer effects. In particular, among various stimuli-sensitive drug carriers, pH-sensitive drug carriers are being studied by targeting the acidity of cancer tissues or cancer cell endosomal pH (W. Park, et al., *J. Ameri. Chem. Soc.* 138 (34), 10734-10737). The pH around cancer is more acidic than normal tissues (pH<7.0), and this acidification is dependent on the size and distribution of the cancer (E S Lee, et al., *J. Control. Release*, 123 (1), 19-26).

These drug carriers using the pH of cancer tissues conventionally use substances such as chitosan, piperidine, imidazole, histidine, lysine and glutamic acid. In addition, pH-sensitive drug carriers are prepared by inducing pH-sensitive binding such as hydrazine, oxime and acetal. However, it is inevitable to synthesize a pH-sensitive drug carrier using the above substance. This is because a pH-sensitive drug carrier is prepared by polymerizing above substance or synthesizing it with a polymer in order to impart a pH-sensitive site. In addition, since the step of synthesizing the pH-sensitive polymer proceeds through several steps, there are problems such as cost, time and synthesis yield. Therefore, it is necessary to prepare a non-polymeric pH-sensitive drug carrier capable of preparing a pH-sensitive substance in a short time simply.

On the other hand, carbon nanoparticles are spherical particles and have chemical bonds of sp2 and sp3 based on carbon, and are excellent in biocompatibility and safety. In addition, it exhibits fluorescence at a specific wavelength due to the chemical bonds of the carbon nanoparticles. When such carbon nanoparticles are used as a drug carrier or a photodynamic therapeutic agent and the like, biocompatibility and safety can be ensured in vivo, and thus there is an advantage of being used as a safer drug carrier.

Therefore, there is a need for research on technology for simple and fast synthesis preparation of non-polymeric pH-sensitive carbon nanoparticles having biocompatibility and stability and for effective delivery of weakly acidic drug or photodynamic therapy.

DISCLOSURE

Technical Problem

An object of the present invention is to provide non-polymeric pH-sensitive carbon nanoparticles having pH sensitivity.

Also, another object of the present invention is to provide a method of preparing pH-sensitive carbon nanoparticles that can be prepared simply and quickly.

In addition, another object of the present invention is to provide a pH-sensitive carbon nanoparticle-based drug carrier that the drug can be encapsulated in the pH-sensitive carbon nanoparticles and released under weakly acidic conditions, so that it can be used for cancer treatment, photodynamic therapy, or photo-mediated anticancer immunotherapy.

Technical Solution

In order to achieve the above object, the present invention provides pH-sensitive carbon nanoparticles comprising imidazole.

Also, the present invention provides a drug carrier comprising the pH-sensitive carbon nanoparticles and a drug capable being encapsulated in the nanoparticles.

In addition, the present invention provides a method of preparing pH-sensitive carbon nanoparticles comprising: preparing citric acid solution by dissolving citric acid; preparing a mixed solution by adding an imidazole compound to the citric acid solution; preparing carbon nanoparticles by heat-treating the mixed solution; and dialysis and freeze-drying the carbon nanoparticles.

Advantageous Effects

The pH-sensitive nanoparticles according to the present invention can prepare carbon nanoparticles having pH sensitivity by using citric acid and imidazole compounds more simply and quickly than polymeric pH-sensitive nanoparticles.

In addition, the pH-sensitive carbon nanoparticles prepared according to the present invention are biocompatible and have in vivo safety.

Furthermore, the pH-sensitive carbon nanoparticles prepared according to the present invention can encapsulate a hydrophobic drug or a photosensitizer and are capable of releasing the drug under weakly acidic conditions and it can be used as a drug carrier for cancer treatment, photodynamic therapy or photomediated anticancer immunotherapy.

DESCRIPTION OF DRAWINGS

FIG. 1 is a diagram showing the preparation of pH-sensitive carbon nanoparticles using citric acid (CA) and 1-(3-aminopropyl) imidazole (API) in a microwave.

FIG. 2 is a diagram showing the production of pH-sensitive carbon nanoparticles through a hydrothermal reaction of citric acid and 1-(3-aminopropyl) imidazole in an autoclave.

FIG. 3 shows (A) fluorescence of pH-sensitive carbon nanoparticles prepared according to microwave reaction time, and (B) charge measured at various pHs of pH-sensitive carbon nanoparticles prepared according to microwave reaction time.

FIG. 4 shows the size and charge measured at pH 7.4 and pH 6.5 of pH-sensitive carbon nanoparticles prepared from 6 kinds of compounds (1-(3-aminopropyl) imidazole, 4-imidazole acetic acid hydrochloride, 4-(1H-imidazol-1-yl)-aniline, imidazole, L-histidine and 4-imidazole acrylic acid) in a microwave and the carbon nanoparticles not having pH sensitivity.

FIG. 5 shows the size, the electric charge measured at various pH and each fluorescence image of pH-sensitive carbon nanoparticles prepared through the hydrothermal reaction (4, 8 hours) of 8 kinds of compounds (1-(3-aminopropyl) imidazole, 4-imidazole acetic acid hydrochloride, 4-(1H-imidazol-1-yl)-aniline, imidazole, L-histidine (4, 8 hours), 4-imidazole acrylic acid).

FIG. 6 shows the size, the charge measured at various pHs and fluorescence images of pH-sensitive carbon nanoparticles prepared through an autoclave of 1-(3-aminopropyl) imidazole.

FIG. 7 shows the particle size and results of transmission electron microscope measured at pH 7.4 and pH 6.5 of drug carriers based on pH-sensitive carbon nanoparticles of 6 kinds of doxorubicin-encapsulated compounds (1-(3-aminopropyl) imidazole, 4-imidazole acrylic acid, 4-imidazole acetic acid hydrochloride, 4-(1H-imidazol-1-yl)-aniline, imidazole, L-histidine).

FIG. 8 shows the drug release according to the pH of drug carriers based on pH-sensitive carbon nanoparticles of 6 kinds of doxorubicin-encapsulated compounds (1-(3-aminopropyl) imidazole, 4-imidazole acrylic acid, 4-imidazole acetic acid hydrochloride, 4-(1H-imidazol-1-yl)-aniline, imidazole, L-histidine).

FIG. 9 shows an X-ray photoelectron spectroscopy (XPS) analysis of pH-sensitive carbon nanoparticles prepared using CA and API.

FIG. 10 shows the minimum concentrations at which drug carriers are produced by hydrophobic drug binding at pH 7.4 and pH 6.5.

FIG. 11 shows the particle changes at pH 7.4 and pH 6.5 of a CA and API-based pH-sensitive carbon nanoparticle drug carrier in which doxorubicin is encapsulated.

FIG. 12 shows the particle changes at various pHs of a CA and API-based pH-sensitive carbon nanoparticle drug carrier in which doxorubicin is encapsulated.

FIG. 13 shows the evaluation of normal cytotoxicity of a CA and API-based pH-sensitive carbon nanoparticle drug carrier.

FIG. 14 shows the effect of killing cancer cells of a CA and API-based pH-sensitive carbon nanoparticle drug carrier in which doxorubicin is encapsulated.

FIG. 15 shows (A) to (C) illustrating the effect of influx of a CA and API-based pH-sensitive carbon nanoparticle drug carrier in which doxorubicin is encapsulated into cancer cells at pH 7.4 (B) and pH 6.5 (C).

FIG. 16 shows (A) and (B) illustrating the anticancer effect in vivo of a CA and API-based pH-sensitive carbon nanoparticle drug carrier in which doxorubicin is encapsulated and (C) illustrating the evaluation of the in vivo toxicity of the carrier.

FIG. 17 shows the anticancer effect through in vivo cancer tissue staining of a CA and API-based pH-sensitive carbon nanoparticle drug carrier in which doxorubicin is encapsulated.

FIG. 18 shows (A) illustrating a method of preparing a photodynamic therapeutic agent based on a pH-sensitive carbon nanoparticle in which a photosensitizer material is encapsulated and (B) illustrating a change in the therapeutic agent at pH 7.4 and 6.5.

FIG. 19 shows the particle changes at pH 7.4 and pH 6.5 of a pH-sensitive carbon nanoparticle-based photodynamic therapeutic agent in which a photosensitizer is encapsulated.

FIG. 20 shows the charge at pH 7.4 and pH 6.5 of a pH-sensitive carbon nanoparticle-based photodynamic therapeutic agent in which a photosensitizer is encapsulated.

FIG. 21 shows (A) illustrating the evaluation of the active oxygen generation ability of a pH-sensitive carbon nanoparticle-based photodynamic therapeutic agent in which a photosensitizer (Ce6, Pheo a) is encapsulated and (B) illustrating the evaluation of the active oxygen generation ability at pH 7.4 and 6.5 of a pH-sensitive carbon nanoparticle-based photodynamic therapeutic agent in which a photosensitizer is encapsulated compared to that of a photosensitizer alone.

FIG. 22 shows the particle changes at various pHs of a pH-sensitive carbon nanoparticle-based photodynamic therapeutic agent in which a photosensitizer is encapsulated.

FIG. 23 shows (A) and (B) illustrating the drug release according to pH of a pH-sensitive carbon nanoparticle-based photodynamic therapeutic agent in which a photosensitizer is encapsulated.

FIG. 24 is a diagram showing the effect of influx into cancer cells at pH 7.4 and pH 6.5 of a pH-sensitive carbon nanoparticle-based photodynamic therapeutic agent in which a photosensitizer is encapsulated.

FIG. 25 shows the effect of killing cancer cells at pH 6.5 of a pH-sensitive carbon nanoparticle-based photodynamic therapeutic agent in which a photosensitizer is encapsulated.

FIG. 26 shows (A), (B) and (C) illustrating in vivo behavior evaluation of a pH-sensitive carbon nanoparticle-based photodynamic therapeutic agent in which a photosensitizer is encapsulated.

FIG. 27 shows (A) illustrating the in vivo photodynamic anticancer effect and immuno-anticancer effect of a pH-sensitive carbon nanoparticle-based photodynamic therapeutic agent in which a photosensitizer is encapsulated and (B) illustrating the toxicity evaluation in vivo thereof.

FIG. 28 shows the effect of inducing photodynamic mediated immune cells in vivo of a pH-sensitive carbon nanoparticle-based photodynamic therapeutic agent in which a photosensitizer is encapsulated.

FIG. 29 shows the anticancer effect of a pH-sensitive carbon nanoparticle-based photodynamic therapeutic agent in which a photosensitizer is encapsulated through in vivo cancer tissue staining.

FIG. 30 shows the effect of inducing photodynamic mediated immune cell of a pH-sensitive carbon nanoparticle-based photodynamic therapeutic agent in which a photosensitizer is encapsulated through in vivo cancer tissue staining.

BEST MODE

Hereinafter, the present invention will be described in detail.

The present inventors have prepared a pH-sensitive carbon nanoparticle containing an imidazole functional group in the carbon nanoparticle by a microwave, hydrothermal reaction or autoclave reaction using citric acid and imidazole compounds simply and quickly and they have found that these pH-sensitive carbon nanoparticles can encapsulate drugs and are excellent in drug release ability under weakly acidic conditions, and can be used as drug carriers for cancer treatment, photodynamic therapy, or photomediated anticancer immunotherapy, and have completed the present invention.

The present invention provides pH-sensitive carbon nanoparticles comprising imidazole.

At this time, the pH-sensitive carbon nanoparticles are prepared using citric acid and imidazole compounds, and the imidazole compound may be at least one selected from the group consisting of 1-(3-aminopropyl) imidazole, 4-imidazole acetic acid hydrochloride, 4-(1H-imidazole-1-yl)-aniline, imidazole, L-histidine and 4-imidazoleacrylic acid, and preferably it may be 1-(3-aminopropyl) imidazole.

According to an embodiment of the present invention, the pH-sensitive carbon nanoparticles may have an average particle size of 2 to 10 nm, and may have a negative charge at pH≥7.0, and a neutral charge or positive charge at pH<7.0.

In addition, the present invention provides a drug carrier comprising the pH-sensitive carbon nanoparticles and a drug capable being encapsulated in the nanoparticles.

At this time, the drug may be at least one selected from the group consisting of a hydrophobic drug, a chlorine-based drug and a porphyrin-based drug, and the drugs may be at least one anticancer agent selected from the group consisting of doxorubicin, paclitaxel, cisplatin, sirolimus and etoposide, or at least one photosensitizer selected from the group consisting of chlorine e6, pheophorbide a and phthalocyanine, but it is limited thereto.

According to an embodiment of the present invention, the weight ratio of the carbon nanoparticles and the drug may be 1:1 to 15:1, and the average particle size of the drug carrier may be 50 to 250 nm.

In addition, the drug carrier may be destabilized in a weakly acidic environment of pH 7.0 or less, that is, the structure of the drug carrier is changed, so that the drug encapsulated in the drug carrier may be released to the outside.

Therefore, the drug carrier in the present invention is effectively used for drug release at about pH 6.0 to 7.0, which is a weakly acidic condition formed at a disease site such as cancer, and thus can be used for cancer treatment, photodynamic therapy or photomediated anticancer immunotherapy.

According to an embodiment of the present invention, it was confirmed that the pH-sensitive carbon nanoparticle drug carrier in which doxorubicin anticancer agent is encapsulated has superior cancer growth inhibition and cancer cell killing effects in vivo than a single doxorubicin formulation.

In addition, it was confirmed that the pH-sensitive carbon nanoparticles photodynamic therapeutic agent in which chlorine e6 photosensitizer is encapsulated has superior accumulation in cancer tissues, cancer growth inhibition and the effect of killing cancer cells in vivo than a single chlorine e6 formulation.

In addition, it was confirmed that the photodynamic therapeutic agent of the present invention exhibits an immune anticancer effect induced by photodynamic therapy, and thus cancer growth can be inhibited even on the other side of cancerous tissue that has not been irradiated with laser.

In addition, the present invention provides a method of preparing pH-sensitive carbon nanoparticles comprising: preparing citric acid solution by dissolving citric acid; preparing a mixed solution by adding an imidazole compound to the citric acid solution; preparing carbon nanoparticles by heat-treating the mixed solution; and dialysis and freeze-drying the carbon nanoparticles.

At this time, the imidazole compound may be at least one selected from the group consisting of 1-(3-aminopropyl) imidazole, 4-imidazole acetic acid hydrochloride, 4-(1H-imidazole-1-yl)-aniline, imidazole, L-histidine and 4-imidazoleacrylic acid, and preferably it may be 1-(3-aminopropyl) imidazole).

In addition, the mixed solution may be heat-treated by at least one selected from the group consisting of a microwave pyrolysis reaction, a hydrothermal reaction and an autoclave reaction.

In this case, the microwave pyrolysis reaction may be performed for 1 to 5 minutes, preferably for 3 minutes in a microwave.

In addition, the hydrothermal reaction may be performed for 4 to 8 hours in an oil bath at 100 to 200° C., preferably for 4 hours in an oil bath at 180° C.

In addition, the autoclave reaction may be performed for 8 to 12 hours in an autoclave at 100 to 150° C., preferably, for 8 hours in an autoclave at 120° C.

At this time, if the heat treatment is performed under conditions out of the above, the carbon nanoparticles having an imidazole structure formed on the surface are not properly formed, so that the pH-sensitive carbon nanoparticles according to the present invention cannot be formed and a problem that cannot be used as a drug carrier for photomediated immuno-cancer therapy may be caused.

According to an embodiment of the present invention, the average particle size of the pH-sensitive carbon nanoparticles prepared through the heat treatment reaction is 2 to 10 nm, and may have a negative charge at pH≥7.0 and a neutral charge or positive charge at pH<7.0.

A pH-sensitive photodynamic therapeutic agent was prepared by encapsulation by hydrophobic interaction between the photosensitizer and the central part of the carbon nanoparticles at pH 8 (FIG. 18A) and at pH 7.4, the shape of the nanoparticle drug carrier was maintained, while at pH 6.5, as the charge of the API with a pKa value of 6.9 changes, the hydrophobic central part changes to hydrophilic and the balance between hydrophobicity and hydrophilicity is destroyed and the shape of the drug carrier collapses, and the encapsulated photosensitizer is released out of the particle (FIG. 18B), and thus it can be used as a cancer-selective drug carrier, a photodynamic therapeutic agent or a photomediated anticancer immunotherapeutic agent.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

<Example 1> Preparation of pH-Sensitive Carbon Nanoparticles Through Microwave

A pH-sensitive carbon nanoparticle was prepared using citric acid (CA) and 1-(3-aminopropyl) imidazole (API) as shown in FIG. 1. Specifically, 1 g of citric acid was added to an Erlenmeyer flask and 5 ml of water was added to dissolve it. Then, 1-(3-aminopropyl) imidazole was added to the solution at a concentration of 4 mol of citric acid, respectively. After mixing the solution well and putting in a microwave oven (1100 W) and it was operated for 3 minutes to prepare carbon nanoparticles through microwave assistant pyrolysis.

In the same method as above, instead of API, 4-imidazoleacetic acid hydrochloride, 4-(1H-imidazol-1-yl)-aniline, imidazole, L-histidine and 4-imidazole acrylic acid were used to prepare a total of six pH-sensitive carbon nanoparticles. The prepared carbon nanoparticles were purified in distilled water through a dialysis membrane (500 Da) for one day, and then changed twice with clean distilled water. One day after dialysis, the solution in the dialysis membrane was lyophilized to recover six pH-sensitive carbon nanoparticles.

<Example 2> Preparation Through Hydrothermal Reaction of pH-Sensitive Carbon Nanoparticles A pH-sensitive carbon nanoparticle was prepared using citric acid (CA) and 1-(3-aminopropyl) imidazole (API) as shown in FIG. 2.

Specifically, 1 g of citric acid was added to a Teflon reactor chamber, and 5 ml of water was added to dissolve it. Then, 1-(3-aminopropyl) imidazole was added to the solution at a concentration of 4 mol of citric acid, respectively. After mixing the solution well, the Teflon reaction chamber was placed in a stainless steel reactor and placed in an oil bath at 180° C. for 4 hours to prepare carbon nanoparticles through hydrothermal synthesis.

In the same method as above, instead of API, 4-imidazoleacetic acid hydrochloride, 4-(1H-imidazol-1-yl)-aniline, imidazole, L-histidine and 4-imidazole acrylic acid were used to prepare a total of six pH-sensitive carbon nanoparticles. The prepared carbon nanoparticles were purified in distilled water through a dialysis membrane (500 Da) for one day, and then changed twice with clean distilled water. One day after dialysis, the solution in the dialysis membrane was lyophilized to recover six pH-sensitive carbon nanoparticles.

<Example 3> Preparation of pH-Sensitive Carbon Nanoparticles Through Autoclave

A pH-sensitive carbon nanoparticles was prepared using citric acid (CA) and 1-(3-aminopropyl) imidazole (API) as shown in FIG. 2.

Specifically, 1 g of citric acid was added to a Teflon reactor chamber, and 5 ml of water was added to dissolve it. Then, 1-(3-aminopropyl) imidazole) was added to the solution at a concentration of 4 mol of citric acid, respectively. After mixing the solution well, the Teflon reaction chamber was placed in a stainless steel reactor and pH-sensitive carbon nanoparticles were prepared using an autoclave at 120° C. for 8 hours. The prepared carbon nanoparticles were purified in distilled water through a dialysis membrane (500 Da) for one day, and then changed twice with clean distilled water. One day after dialysis, the solution in the dialysis membrane was lyophilized to recover the pH-sensitive carbon nanoparticles.

<Example 4> Preparation of Drug Carrier Based on pH-Sensitive Carbon Nanoparticles Encapsulated with Doxorubicin In order to prepare a pH-sensitive drug carrier, 130 mg of pH-sensitive carbon nanoparticles prepared in Example 1 and 10 mg of doxorubicin were dissolved in 10 ml in dimethyl sulfoxide, respectively. Thereafter, the two dissolved solutions were mixed to prepare nanoparticles in distilled water through a dialysis membrane (3000 Da). When preparing nanoparticles through a dialysis membrane, the pH was adjusted to 8.0 using NaOH, and then the mixture was replaced with clean distilled water twice a day. One day later, the solution in the dialysis membrane was recovered, and the aggregated particles were removed through a syringe filter (0.2 μm), and a centricorn (10000 Da) was used in a centrifuge for 20 minutes at 4000 RPM to remove unencapsulated doxorubicin.

<Example 5> Preparation of pH-Sensitive Carbon Nanoparticle-Based Photodynamic Therapeutic Agent and Photomediated Anticancer Immunotherapeutic Agent In order to prepare a pH-sensitive photodynamic therapeutic agent, 100 mg of pH-sensitive carbon nanoparticles prepared using CA and API in Example 1 and 10 mg of chlorine-based chlorine e6 (Ce6) or porphyrin-based pheophorbide a (Pheo a) were dissolved in 10 ml of dimethyl sulfoxide, respectively. Thereafter, the pH-sensitive carbon nanoparticles were mixed with a Ce6 or pheo a solution to prepare nanoparticles in distilled water through a dialysis membrane (3000 Da). When preparing nanoparticles through a dialysis membrane, the pH was adjusted to 8.0 using NaOH, and the mixture was replaced with clean distilled water twice a day. One day later, the solution in the dialysis membrane was recovered, and the aggregated particles were removed through a syringe filter (0.2 μm), and a centricorn (10000 Da) was used in a centrifuge for 20 minutes at 4000 RPM to remove unencapsulated ce6 or pheo a.

COMPARATIVE EXAMPLE 1

Preparation of Carbon Nanoparticles Not Sensitive to pH

In order to prepare carbon nanoparticles that do not have pH sensitivity, CA, glycerol and cysteamine were used.

Specifically, 1 g of citric acid was added to an Erlenmeyer flask and 5 ml of water was added to dissolve it. Then, 10 ml of glycerol and 0.5 g of cysteamine were added to the solution. After mixing the solution well and putting it in a microwave oven (1100 W) and it was operated for 3 minutes to prepare carbon nanoparticles through microwave assistant pyrolysis. The prepared carbon nanoparticles were purified in distilled water through a dialysis membrane (500 Da) for one day, and then changed twice with clean distilled water. One day after dialysis, the solution in the dialysis membrane was lyophilized to recover carbon nanoparticles that do not have pH sensitivity.

<Experimental Example 1> Setting of Preparation Conditions Through Microwave of pH-Sensitive Carbon Nanoparticles The pH-sensitive carbon nanoparticles produced through the microwave assistant pyrolysis have various production efficiency of carbon nanoparticles depending on the energy of the microwave wavelength of the microwave oven, and thus to set the production conditions for the pH-sensitive carbon nanoparticles, pH-sensitive carbon nanoparticles were prepared by setting microwaves under three conditions of 1 minute, 3 minutes and 5 minutes.

Specifically, 1 g of citric acid was added to an Erlenmeyer flask and 5 ml of water was added to dissolve it. Then, API was added to the solution at a concentration of 4 mol of CA. After mixing the solution well and putting it in a microwave oven (1100 W), it was operated for 1, 3 and 5 minutes, respectively, to prepare carbon nanoparticles through microwave assistant pyrolysis.

The fluorescence of the pH-sensitive carbon nanoparticles prepared as the above was visually compared with the naked eye under UV (335 nm) conditions, and purified for a day through a dialysis membrane (500 Da) in distilled water, and then replaced with clean distilled water twice. One day after dialysis, the solution in the dialysis membrane was lyophilized to recover pH-sensitive carbon nanoparticles under three conditions. The recovered pH-sensitive carbon nanoparticles were evaluated for pH sensitivity by measuring the surface charge at each pH.

As a result of the experiment, as shown in FIG. 3A, the strongest fluorescence was displayed at 3 minutes, and as shown in FIG. 3B, a positive charge was displayed at pH 6.5 in a cancer environment. However, when exposed to microwave for 1 minute, carbon nanoparticles are not produced properly due to low energy. When exposed for 5 minutes, the imidazole structure is greatly collapsed due to too much energy, resulting that the pH-sensitive carbon nanoparticles were not properly prepared.

Hereinafter, the pH-sensitive carbon nanoparticles were prepared under a microwave reaction for 3 minutes, and an experiment was performed.

<Experimental Example 2> Measurement of Size and Surface Charge of pH-Sensitive Carbon Nanoparticles Prepared Through Microwave The pH-sensitive carbon nanoparticles of 6 kinds (1-(3-aminopropyl) imidazole, 4-imidazole acetic acid hydrochloride, 4-(1H-imidazol-1-yl)-aniline, to imidazole, L-histidine, 4-imidazole acrylic acid) prepared in Example 1 were dissolved in distilled water at a concentration of 1 mg/ml, and then the size of the nanoparticles was measured through a zeta potential particle size analyzer. In addition, in order to check the change of the surface charge of the nanoparticles according to the pH, the charge was measured through a zeta potential particle size analyzer at various pHs by adjusting the pH using 1 N HCl and NaOH. As a comparative group, carbon nanoparticles not sensitive to pH (Comparative Example 1) were measured in the same manner as described above.

As for the pH-sensitive carbon nanoparticles of 6 kinds (1-(3-aminopropyl) imidazole, 4-imidazole acetic acid hydrochloride, 4-(1H-imidazol-1-yl)-aniline, imidazole, L-histidine, 4-imidazole acrylic acid) and the carbon nanoparticles not sensitive to the pH (cysteamine; cysteamine) of Comparative Example 1, it was confirmed that both had a size of about 5 nm, as shown in FIG. 4.

In addition, as a result of confirming the surface charge, as shown in FIG. 4, it was confirmed that the body had a negative charge at pH 7.4, the pH in vivo and the positive (+) charge at pH ~6.5, the pH under cancer environment. On the other hand, in the case of carbon nanoparticles that are not sensitive to pH (Comparative Example 1), it was confirmed that the particle size was similar to that of the pH sensitive carbon nanoparticles, but continued to show negative (−) charge regardless of the pH.

<Experimental Example 3> Measurement of Size, Surface Charge, and Fluorescence Intensity of pH-Sensitive Carbon Nanoparticles Prepared Through Hydrothermal Reaction The pH-sensitive carbon nanoparticles of eight kinds (1-(3-aminopropyl) imidazole, 4-imidazole acetic acid hydrochloride, 4-(1H-imidazol-1-yl)-aniline, imidazole, L-histidine (4, 8 hours), 4-(imidazole acrylic acid)) (4, 8 hours) prepared in Example 2 were dissolved in distilled water at a concentration of 10 mg/ml, and the size of the nanoparticles was measured through a zeta potential particle size analyzer. In addition, in order to check the change of the surface charge of the nanoparticles according to the pH, the charge was measured through a zeta potential particle size analyzer at various pHs by adjusting the pH using 1 N HCl and NaOH. In addition, the fluorescence intensity of the prepared pH-sensitive carbon nanoparticles was measured using an in vivo fluorescence imaging (fluorescence-labeled bioimaging instrument).

As for the pH-sensitive carbon nanoparticles of eight kinds (1-(3-aminopropyl) imidazole, 4-imidazole acetic acid hydrochloride, 4-(1H-imidazol-1-yl)-aniline, imidazole, L-histidine (4, 8 hours), 4-(imidazole acrylic acid)) (4, 8 hours), it was confirmed that all of them had a size of about 4 nm as in FIG. 5.

In addition, as a result of confirming the surface charge, it was confirmed that there was no negative (−) charge or charge at the pH 7.4, the pH in vivo, and the charge increased or had positive (+) charge at the pH ~6.5, the pH in the cancer environment. In addition, as a result of measuring the fluorescence of each of the prepared carbon nanoparticles, it was confirmed that all of them exhibited strong fluorescence.

<Experimental Example 4> Measurement of Size and Surface Charge of pH-Sensitive Carbon Nanoparticles Prepared Through Autoclave After dissolving 1-(3-aminopropyl) imidazole-based pH-sensitive carbon nanoparticles prepared in Example 3 at a concentration of 10 mg/ml in distilled water, the size of the nanoparticles was measured through a zeta potential particle size analyzer. In addition, in order to check the change of the surface charge of the nanoparticles according to the pH, the charge was measured through a zeta potential particle size analyzer at various pHs by adjusting the pH using 1 N HCl and NaOH. In addition, the fluorescence intensity of the prepared pH-sensitive carbon nanoparticles was measured using an in vivo fluorescence imaging (fluorescence-labeled bioimaging instrument).

As a result of confirming the above prepared pH-sensitive carbon nanoparticles, it was confirmed to have a size of about 3 nm as shown in FIG. 6.

In addition, as a result of confirming the surface charge, it was confirmed that as shown in FIG. 6, it had a negative (−) charge at pH 7.4, the pH in vivo, and had positive (+) charge at the pH ~6.5, the pH in the cancer environment. In addition, as a result of measuring the fluorescence of the produced carbon nanoparticles, it was confirmed that it exhibited strong fluorescence.

<Experimental Example 5> Confirmation of Particles of Drug Carrier Based on pH-Sensitive Carbon Nanoparticles Encapsulated with Doxorubicin The particle size of the drug carrier based on the pH-sensitive carbon nanoparticle encapsulated with doxorubicin of six kinds (1-(3-aminopropyl) imidazole, 4-imidazole acetic acid hydrochloride, 4-(1H-imidazol-1-yl)-aniline, imidazole, L-histidine, 4-imidazole acrylic acid) prepared in Example 4 was confirmed through a zeta potential particle size analyzer and a transmission electron microscope. Each was measured after dissolving in distilled water at a concentration of 1 mg/ml, and it was confirmed by a transmission electron microscope at two pH levels, pH 7.4 and pH 6.5.

As a result, as shown in FIG. 7, it was found that six types of drug carriers based on the pH-sensitive carbon nanoparticles encapsulated with doxorubicin have a size of about 70 nm. As a result of checking with a transmission electron microscope, it was confirmed that the shape of the nanoparticle drug carrier was maintained at pH 7.4, while the shape of the drug carrier was collapsed at pH 6.5.

<Experimental Example 6> Drug Release Experiment According to pH of Drug Carrier Based on pH-Sensitive Carbon Nanoparticles The drug release experiments of the drug carrier based on the pH-sensitive carbon nanoparticle encapsulated with doxorubicin of six kinds (1-(3-aminopropyl) imidazole, 4-imidazole acetic acid hydrochloride, 4-(1H-imidazol-1-yl)-aniline, imidazole, L-histidine, 4-imidazole acrylic acid) prepared in Example 4 were performed using a drug release kit (MWCO 10K) in PBST (0.01M, tween 80 1%) of pH 7.4, pH 6.5.

As a result, it was confirmed that the pH-sensitive carbon nanoparticle-based drug carrier prepared using CA and API was released up to about 70% at pH 6.5 to release the most drugs, as shown in FIG. 8.

Hereinafter, additional experiments were performed on the pH-sensitive carbon nanoparticles and drug carriers prepared using CA and API.

<Experimental Example 7> Confirmation of Surface Functional Groups of pH-Sensitive Carbon Nanoparticle The imidazole functional group on the surface of the pH-sensitive carbon nanoparticles prepared using CA and API was confirmed through X-ray photoelectron spectroscopy (XPS).

As a result, as shown in FIG. 9, three elements of C, N and O exist in total, and as a result of an N1s spectrum analysis, N—H and C=N—C bonds present in the pyrrole were confirmed. Through this, it was found that the imidazole functional group is present on the surface of the carbon nanoparticles without breaking.

<Experimental Example 8> Confirmation of the Minimum Concentration of Drug Carrier Produced by Hydrophobic Binding A hydrophobic fluorescent substance called nile red was used to confirm the minimum concentration of pH-sensitive carbon nanoparticles required when preparing a drug carrier using pH-sensitive carbon nanoparticles. After dissolving nile red in acetone at a concentration of $5 \times 10^{-5}$ M, it was prepared as a thin film using an evaporator. The pH-sensitive carbon nanoparticles prepared with CA and API were dissolved by concentration in distilled water, adjusted to pH 7.4 and 6.5, and then added to the prepared thin film to confirm the formation of the drug carrier through a fluorescence spectrometer. Light was irradiated at 520 nm and detection was measured at 618 nm.

As a result, as shown in FIG. 10, it was confirmed that a drug carrier was formed at a concentration of 0.958 mg/ml or higher at pH 7.4, and a drug carrier was formed at a concentration of 4.090 mg/ml or higher at pH 6.5.

<Experimental Example 9> Confirmation of Particle Change According to pH of pH-Sensitive Carbon Nanoparticle-Based Drug Carrier Particle changes of the CA and API-based pH-sensitive carbon nanoparticle drug carrier encapsulated with doxorubicin prepared in Example 4 were confirmed at pH 7.4 and pH 6.5. After dissolving in distilled water at 1 mg/ml based on doxorubicin, the size was measured through a zeta potential particle size analyzer while repeatedly adjusting the pH to pH 7.4 and pH 6.5 at 5-minute intervals using 0.1 N HCl and NaOH.

As a result, as shown in FIG. 11, it was confirmed that the size was about 70 nm at pH 7.4 and about 1000 nm at pH 6.5.

<Experimental Example 10> Confirmation of Particle Shape According to the pH of pH-Sensitive Carbon Nanoparticle-Based Drug Carrier In order to confirm the change of the particles according to various pHs of the CA and API-based pH-sensitive carbon nanoparticle drug carrier encapsulated with doxorubicin prepared in Example 4, it was dissolved in distilled water at 1 mg/ml based on doxorubicin, after 24 hours, it was visually confirmed with the naked eye.

As a result, as shown in FIG. 12, it was confirmed that the particles were stably maintained at pH 7.0, the pH in vivo or higher, whereas in the case of the cancer environment pH of ~6.5 or less, it was confirmed that the doxorubicin encapsulated in the particles was released out of the particles, resulting in agglomeration and sinking.

<Experimental Example 11> Evaluation of Normal Cytotoxicity of pH-Sensitive Carbon Nanoparticles To evaluate the normal cytotoxicity of the CA and API-based pH-sensitive carbon nanoparticles prepared in Example 1, NIH-3T3 (mouse embryo fibroblast) and L-929 (mouse fibroblast) cells were used. After treating the pH-sensitive carbon nanoparticles by concentration in the pH 7.4 culture solution for 4 hours, the cell death rate after 24 hours was analyzed at 570 nm by MTT assay using a microplate reader.

As a result, as shown in FIG. 13, it is judged that the biocompatibility is excellent because toxicity does not show to 1 mg/ml based on the pH-sensitive carbon nanoparticle concentration in both cells.

<Experimental Example 12> Confirmation of Cancer Cell Killing Efficacy of Drug Carrier Based on pH-Sensitive Carbon Nanoparticles In order to confirm the cancer cell killing effect of the CA and API-based pH-sensitive carbon nanoparticle drug carrier encapsulated with doxorubicin prepared in Example 4, HCT-116 (human colon cancer), SKBR-3 (human breast cancer), PANC-1 (human pancreas cancer) cells were used. The pH-sensitive carbon nanoparticle drug carrier was treated by concentration of doxorubicin in culture solutions of pH 7.4 and pH 6.5, respectively, and the comparison group was comparatively evaluated by treating doxorubicin alone by concentration. Cell death was performed using the MTT assay, and analyzed at 490 nm using a microplate reader.

As a result, as shown in FIG. 14, all cells treated with doxorubicin alone (Free DOX) died at about 50 ug/ml regardless of pH, but the pH-sensitive carbon nanoparticle carrier encapsulated with doxorubicin collapsed at pH 6.5 to show a higher cell death rate than 7.4.

<Experimental Example 13> Confirmation of Effect of Influx of pH-Sensitive Carbon Nanoparticle-Based Drug Carrier into Cells According to pH PANC-1 (Human pancreatic cancer) cells were used to confirm the effect of influx into cancer cells at pH 7.4 and pH 6.5 using the pH-sensitive carbon nanoparticles encapsulated with doxorubicin prepared in the above Example 4. Doxorubicin-encapsulated pH-sensitive carbon nanoparticles were treated for 4 hours in the culture solutions of pH 7.4 and pH 6.5, respectively, and evaluated for comparison. Cell influx was analyzed by fluorescence (460, 590 nm) of carbon nanoparticles (C-dot) and doxorubicin (DOX) using confocal microscopy.

In FIG. 15A, DIC shows the morphology of cells, C-dot and DOX represent each fluorescence, and Merge shows the cell morphology and each fluorescence superimposed.

As a result, it was confirmed by the increase in the intensity of fluorescence (C-dot) and doxorubicin (DOX) of carbon nanoparticles themselves that the degree of influx of doxorubicin encapsulated in the pH-sensitive carbon nanoparticles into the cells was poor at pH 7.4, the pH in vivo as shown in FIG. 15A and FIG. 15B, while as the nanoparticles collapse and the encapsulated doxorubicin is released out of the particles under a cancer environment pH of 6.5 (FIG. 15A and FIG. 15C).

<Experimental Example 14> Confirmation of Inhibitory Effect of pH-Sensitive Carbon Nanoparticle-Based Drug Carrier on Cancer Growth In Vivo In order to confirm the anticancer effect in vivo of the doxorubicin-encapsulated pH-sensitive carbon nanoparticles prepared in Example 4, HCT-116 (Human colon cancer) cells were inoculated subcutaneously ($1 \times 10^7$ cells) of BALB/c mice. When the size of the cancer tissue reaches about 100 mm$^3$, doxorubicin-encapsulated pH-sensitive carbon nanoparticles and doxorubicin alone formulation as a control group, pH-sensitive carbon nanoparticles without drug encapsulation, PBS were intravenously injected at 2 mg/ml based on doxorubicin. After that, the size of the cancer tissue was measured for 15 days to confirm the anticancer effect.

As a result, it was confirmed that cancer continued to grow as a result of intravenous injection of doxorubicin alone, pH-sensitive carbon nanoparticles non-encapsulated with drug, and PBS as shown in FIG. 16A and FIG. 16B, whereas doxorubicin-encapsulated pH-sensitive carbon nanoparticles inhibited greatly cancer cell growth. In addition, as shown in FIG. 16C, except for doxorubicin alone, toxicity in vivo of other formulations did not appear, so it was confirmed that the weight of the rat was constant.

<Experimental Example 15> Confirmation of Anticancer Efficacy Through In Vivo Cancer Tissue Staining of Drug Carrier Based on pH-Sensitive Carbon Nanoparticles In order to confirm the anticancer effect in vivo of the doxorubicin-encapsulated pH-sensitive carbon nanoparticles prepared in Example 4, HCT-116 (Human colon cancer) cells were inoculated subcutaneously ($1 \times 10^7$ cells) to BALB/c mice. When the size of the cancer tissue reaches about 100 mm$^3$, doxorubicin-encapsulated pH-sensitive carbon nanoparticles and doxorubicin alone formulation as a control group, pH-sensitive carbon nanoparticles without drug encapsulation, PBS were intravenously injected at 2 mg/ml based on doxorubicin. After 15 days, the cancer tissue was excised, and cancer cell death was confirmed using the Terminal deoxynucleotidyl transferase dUTP nick end labeling (TUNEL) method and Hematoxylin and eosin stain (H&E) method.

As a result, as shown in FIG. 17, it was confirmed through tissue staining that when doxorubicin-encapsulated pH-sensitive carbon nanoparticles were injected, the killing effect of cancer cells was clearer than doxorubicin alone, pH-sensitive carbon nanoparticles without drug encapsulation, and PBS.

<Experimental Example 16> Confirmation of Particles of Photodynamic Therapeutic Agent Based on pH-Sensitive Carbon Nanoparticles To confirm the change of the particle according to the pH of the particles prepared using a pH-sensitive photodynamic therapeutic agent (FIG. 18) prepared in Example 5 by encapsulation of the photosensitizer by hydrophobic interaction between the photosensitizer and the central part of the carbon nanoparticles at pH 8, it was dissolved in distilled water based on 1 mg/ml of chlorine e6, and then analyzed using a zeta potential particle size analyzer and transmission electron microscope at pH 7.4 and pH 6.5 using 0.1 N HCl and NaOH.

As a result, as shown in FIG. 19, it was found that the particles of the prepared pH-sensitive photodynamic therapeutic agent had a size of about 131 nm, and as a result of confirming with a transmission electron microscope, the shape of the nanoparticle drug carrier was maintained at pH 7.4, whereas as the charge of the API with a pKa value of 6.9 at pH 6.5 was changed, the hydrophobic core portion was changed to hydrophilic, and the balance between hydrophobicity/hydrophilicity was destroyed, and the shape of the drug carrier was confirmed to collapse (FIG. 18B).

<Experimental Example 17> Confirmation of Surface Charge of pH-Sensitive Carbon Nanoparticle-Based Photodynamic Therapeutic Agent In order to check the change of the surface charge of the nanoparticles according to the pH of the particles of the pH-sensitive photodynamic therapeutic agent prepared as in the above Example 5, charge was measured through a zeta potential particle size analyzer at various pHs by adjusting the pH using 1 N HCl and NaOH.

As a result, as shown in FIG. 20, it was confirmed that particles prepared with a pH-sensitive photodynamic therapeutic agent encapsulated with chlorine e6 (Ce6@CDs) have a strong negative (−) charge at pH 7.4, the pH in vivo, or higher, and have a weak negative (−) charge at ~6.5, which is a cancer environment pH.

<Experimental Example 18> Confirmation of Active Oxygen Generation and Active Oxygen Generation Ability According to pH of Photodynamic Therapeutic Agent Based on pH-Sensitive Carbon Nanoparticles A singlet oxygen sensor green (SOSG) capable of detecting singlet oxygen was used to confirm the generation of active oxygen in particles of a pH-sensitive photodynamic therapeutic agent prepared in the above Example 5.

Specifically, 1 ml of a solution in which SOSG was dissolved and 1 ml of a solution in which a pH-sensitive carbon nanoparticle-based photodynamic therapeutic agent was dissolved were mixed, and a 670 nm laser was irradiated. The laser was irradiated with an energy of 20 mW/cm$^2$, and the fluorescence intensity was measured using a fluorescence spectrophotometer every 10 seconds (0.2 J/cm$^2$) to confirm the generation of active oxygen. In addition, in order to measure the efficiency of generating reactive oxygen species according to pH, 1 ml of a solution in which a pH-sensitive photodynamic therapeutic agent having pH 7.4, the pH in vivo and a pH of 6.5 in a cancer environment, was dissolved and 1 ml of a SOSG solution were mixed, and a 670 nm laser is irradiated. The laser was irradiated with an energy of 50 mW/cm$^2$, and the fluorescence intensity was measured using a fluorescence spectrophotometer every 10 seconds (0.5 J/cm$^2$) to confirm the generation of active oxygen species.

As a result, as shown in FIG. 21A, it was confirmed that Pheo A and Ce6, which are present alone, hardly produce singlet oxygen, whereas pH-sensitive carbon nanoparticles encapsulated with each of pheo A and Ce6 efficiently generated singlet oxygen.

In addition, as shown in FIG. 21B, when Ce6 is present alone, it hardly generated singlet oxygen regardless of the presence or absence of a change in pH, whereas in the case of pH-sensitive nanoparticles, it was confirmed that the particles were released at pH 6.5, which is the pH of the cancer environment, to generate singlet oxygen more efficiently than the pH of 7.4 in vivo.

<Experimental Example 19> Confirmation of Particle Change According to pH of pH-Sensitive Carbon Nanoparticle-Based Photodynamic Therapeutic Agent In order to check the change of the particles according to the pH of the pH-sensitive photodynamic therapeutic agent prepared in the above Example 5, 0.5 mg/ml based on chlorine e6 was dissolved in distilled water, and after 24 hours, it was visually confirmed with the naked eyes.

As a result, as shown in FIG. 22, it was confirmed that the particles were stably maintained in the case of pH 7.0~or higher in vivo, whereas in the case of the cancer environment pH of ~6.5 or less, chlorine e6 encapsulated in the particles was released out of the particles, resulting in agglomeration and sinking.

<Experimental Example 20> Drug Release Experiment According to pH of pH-Sensitive Carbon Nanoparticle-Based Photodynamic Therapeutic Agent The drug release experiments of the particles of the pH-sensitive photodynamic therapeutic agent prepared in the above Example were performed using a drug release kit (MWCO 10K) at pH 7.4, pH 6.5 PBST (0.01 M, tween 80 1%).

As a result, as shown in FIG. 23A, the pH-sensitive carbon nanoparticle-based photodynamic therapeutic agent was released up to about 80% at pH 6.5, and the buffer was changed from pH 7.4 to pH 6.5 after 12 hours as shown in FIG. 23B, it was confirmed that the release effect was greatly improved.

<Experimental Example 21> Confirmation of Intracellular Influx Effect of pH-Sensitive Carbon Nanoparticle-Based Photodynamic Therapeutic Agent According to pH In order to confirm the influx effect into cancer cells at pH 7.4 and pH 6.5 using the pH-sensitive photodynamic therapeutic agent prepared in the above Example 5, CT-26 (Mouse colon cancer) cells were used. The pH-sensitive carbon nanoparticle-based photodynamic therapeutic agent was treated for 4 hours in the culture solutions of pH 7.4 and pH 6.5, respectively, and chlorine e6 was treated alone as a control group for comparative evaluation. The intracellular influx was analyzed by fluorescence (460, 665 nm) of carbon nanoparticles and chlorine e6 using confocal microscopy.

As a result, as shown in FIG. 24, it was confirmed indirectly by increasing the fluorescence intensity of carbon nanoparticles themselves (IDCDs) and chlorine e6 (Ce6) that the degree of influx of the chlorine e6 alone treatment group and the pH-sensitive carbon nanoparticle-based photodynamic therapeutic agent into cells was similar at the pH 7.4 in vivo, and on the other hand, in the case of a cancer environment pH of 6.5, the degree of influx into cancer cells increased as the particles collapse and the encapsulated chlorine e6 was released out of the particles.

<Experimental Example 22> Confirmation of Efficacy of pH-Sensitive Carbon Nanoparticle-Based Photodynamic Therapeutic Agent to Kill Cancer Cells at Cancer Environment pH In order to confirm the cancer cell killing effect of the pH-sensitive photodynamic therapeutic agent prepared in the above Example 5 at a cancer environment pH of 6.5, CT-26 (Mouse colon cancer) cells were used. Samples of the pH-sensitive carbon nanoparticle-based photodynamic therapeutic agent and chlorine e6 alone as other comparative group and carbon nanoparticles without pH sensitivity (Comparative Example 1) were treated with 1 µg/ml based on the concentration of chlorine e6 in the pH 6.5 culture medium, equally and a 670 nm laser was irradiated thereto. The laser was irradiated for 20 seconds (2 J/cm$^2$) with an energy of 50 mW/cm$^2$. Cell death was performed using the MTT assay, and analyzed at 570 nm using a microplate reader.

As a result, as shown in FIG. 25, it was confirmed that 50% of the cells treated with chlorine e6 (Free Ce6) alone died in the laser-irradiated group (Free Ce6(+)), but when pH-sensitive carbon nanoparticles encapsulated with chlorine e6 (Ce6@CDs) was irradiated with a laser (Ce6@CDs (+)), it showed a high cell death rate of about 80%.

<Experimental Example 23> Evaluation of In Vivo Behavior of pH-Sensitive Carbon Nanoparticle-Based Photodynamic Therapeutic Agent In order to confirm the in vivo behavior of the pH-sensitive photodynamic therapeutic agent prepared in the above Example 5, CT-26 (Mouse colon cancer) cells were inoculated into BALB/c nude mice. When the size of the cancer tissue reaches about 50-100 mm$^3$, a pH-sensitive photodynamic therapeutic agent (Ce6@CDs) and chlorine e6 alone formulation (Free Ce6) as a comparative group were injected intravenously at 0.4 mg/ml based on chlorine e6, and for 24 hours after then, the in vivo behavior was confirmed using in vivo fluorescence imaging (fluorescence-labeled bioimaging instrument) hourly.

As a result, as shown in FIG. 26A, it was confirmed that fluorescence quickly disappeared by the in vivo elimination system in the comparative group injected with chlorine e6 alone, whereas the pH-sensitive photodynamic therapeutic agent was accumulated in cancer tissues due to the enhanced permeability and retention effect (EPR effect) which are characteristic of the nanoparticles and remained even after 24 hours. In addition, as shown in FIG. 26B and FIG. 26C, after 24 hours, major organs (Liver, Heart, Lung, Spleen, Kidney) and cancer tissues (Tumor) were excised, observed for fluorescence, and quantified and the pH-sensitive photodynamic therapeutic agent was accumulated about 4 times more in cancer tissues than chlorine e6 alone.

<Experimental Example 24> Confirmation of In Vivo Photodynamic Anticancer Effect and Immune Anticancer Effect of pH-Sensitive Carbon Nanoparticle-Based Photodynamic Therapeutic Agent In order to confirm the anticancer effect in vivo and the anticancer effect due to photodynamic-based immunity induction of the pH-sensitive photodynamic therapeutic agent prepared in the above Example 5, CT-26 (Mouse colon cancer) cells were inoculated subcutaneously in the left leg of BALB/c mice ($1\times10^6$ cells) and the right leg ($5\times10^5$ cells). When the size of the cancer tissue reaches about 50 mm$^3$, a pH-sensitive photodynamic therapeutic agent, chlorine e6 alone formulation as a comparative group, pH-sensitive carbon nanoparticles without drug encapsulation, and PBS were injected intravenously at 0.4 mg/ml based on chlorine e6, and after 24 hours after intravenous injection, only the left cancer tissue was irradiated with a laser. This was repeated twice, and the laser was irradiated for 1000 seconds (100 J/cm$^2$) with an energy of 100 mW/cm$^2$. By measuring the size of both cancer tissues for 15 days, the photodynamic anticancer effect and the resulting immune anti-cancer effect were confirmed.

As a result, as shown in FIG. 27A, as a result of intravenous injection of chlorine e6 (Free Ce6) alone, pH-sensitive carbon nanoparticles without drug encapsulation, and PBS, cancer rapidly grows regardless of laser irradiation. On the other hand, when the pH-sensitive photodynamic therapeutic agent was irradiated with a laser (Ce6@CDs(+)), it was confirmed that the photodynamic-mediated anticancer effect of the left cancer was observed, and cancer cell growth was greatly inhibited. In addition, it was confirmed that the cancer cell growth was inhibited in the right cancer despite not being irradiated with laser due to the immune anticancer effect induced by photodynamic therapy. In addition, as shown in FIG. 27B, it was confirmed that the weight of the rat was constant because the toxicity in vivo of each formulation did not appear <Experimental Example 25> Confirmation of Photodynamic-Based Immune Cell Induction of pH-Sensitive Carbon Nanoparticle-Based Photodynamic Therapeutic Agent In order to confirm the photodynamic-based immune induction of the pH-sensitive photodynamic therapeutic agent prepared in the above Example 5, CT-26 (Mouse colon cancer) cells were inoculated subcutaneously in the left leg ($1\times10^6$ cells) and the right leg ($5\times10^5$ cells). When the size of the cancer tissue reaches about 50 mm$^3$, a pH-sensitive photodynamic therapeutic agent, chlorine e6 alone formulation as a comparative group, pH-sensitive carbon nanoparticles without drug encapsulation, and PBS were injected intravenously at 0.4 mg/ml based on chlorine e6, and after 24 hours after intravenous injection, only the left cancer tissue was irradiated with a laser. This was repeated twice, and the laser was irradiated for 1000 seconds (100 J/cm$^2$) with an energy of 100 mW/cm$^2$. After 5 days, the distribution of cytotoxic T cells that penetrated the cancer tissue by removing cancer tissue from each mouse was confirmed by flow cytometry using Anti-CD3 and Anti-CD8 antibodies.

As a result, as shown in FIG. 28, it was confirmed that immune cells in the left cancer irradiated with a laser on a pH-sensitive photodynamic therapeutic agent (Ce6@CDs) were induced about at least 10 times more than the case in which chlorine e6 (Ce6) alone, pH-sensitive carbon nanoparticles without drug encapsulation, and PBS were intravenously injected and irradiated with laser. In addition, in the case of the right cancer of the pH-sensitive photodynamic therapeutic agent without laser irradiation, the photodynamic-based immunity induction effect was observed to confirm that approximately three times more immune cells were induced than when irradiated with laser after chlorine e6 injection alone.

<Experimental Example 26> Confirmation of Anticancer Efficacy Through In Vivo Cancer Tissue Staining of pH-Sensitive Carbon Nanoparticle-Based Photodynamic Therapeutic Agent In order to confirm the anticancer efficacy of the pH-sensitive photodynamic therapeutic agent prepared in the above Example 5 in cancer tissues, CT-26 (Mouse colon cancer) cells were inoculated into BALB/c mice. When the size of the cancer tissue reaches about 50 mm$^3$, a pH-sensitive photodynamic therapeutic agent, chlorine e6 alone formulation as a comparative group, pH-sensitive carbon nanoparticles without drug encapsulation, and PBS were injected intravenously at 0.4 mg/ml based on chlorine e6, and after 24 hours after intravenous injection, only the left cancer tissue was irradiated with a laser. This was repeated twice, and the laser was irradiated for 1000 seconds (100 J/cm$^2$) with an energy of 100 mW/cm$^2$. After 15 days, the cancer tissue was excised, and cancer cell death was confirmed using the Terminal deoxynucleotidyl transferase dUTP nick end labeling (TUNEL) method and Hematoxylin and eosin stain (H&E) method.

As a result, as shown in FIG. 29, the killing effect of cancer cells in the case of cancer irradiated with a laser on a pH-sensitive photodynamic therapeutic agent, was more pronounced than the case in which chlorine e6 (Ce6) alone, pH-sensitive carbon nanoparticles without drug encapsulation (Carbon dots), and PBS were intravenously injected and irradiated with laser.

<Experimental Example 27> Confirmation of Immune Cells Induced in Cancer Tissues of pH-Sensitive Carbon Nanoparticle-Based Photodynamic Therapeutic Agent In order to confirm the induced immune cells in cancer tissues of the pH-sensitive photodynamic therapy prepared in Example 5, CT-26 (Mouse colon cancer) cells were inoculated into BALB/c mice. When the size of the cancer tissue reaches about 50 mm$^3$, a pH-sensitive photodynamic therapeutic agent, chlorine e6 alone formulation as a comparative group, pH-sensitive carbon nanoparticles without drug encapsulation, and PBS were injected intravenously at 0.4 mg/ml based on chlorine e6, and after 24 hours after intravenous injection, only the left cancer tissue was irradiated with a laser. This was repeated twice, and the laser was irradiated for 1000 seconds (100 J/cm$^2$) with an energy of 100 mW/cm$^2$. After 15 days, the cancer tissue was excised, and immune cells induced into the cancer tissue were confirmed using the Immunohistochemistry method.

As a result, as shown in FIG. 30, the distribution of T cells and NK cells induced into cancer tissues in the case of cancer irradiated with a laser on a pH-sensitive photodynamic therapeutic agent, was superior to than the case in which chlorine e6 (Ce6) alone, pH-sensitive carbon nanoparticles without drug encapsulation (Carbon dots), and PBS were intravenously injected and irradiated with laser.

Through this, the pH-sensitive nanoparticles according to the present invention encapsulate a hydrophobic drug or a photosensitizer inside thereof and can release a hydrophobic drug or a photosensitizer at a weakly acidic pH and thus it was confirmed that it can be used as a cancer-selective drug carrier, a photodynamic therapeutic agent, or a photomediated anticancer immunotherapeutic agent.

The invention claimed is:

1. A drug carrier comprising pH-sensitive carbon nanoparticles and a hydrophobic drug capable being encapsulated in the nanoparticles,
    wherein the pH-sensitive carbon nanoparticles comprise:
        citric acid; and
        at least one imidazole compound selected from the group consisting of 1-(3-aminopropyl) imidazole, 4-imidazoleacetic acid hydrochloride, 4-(1H-imidazole-1-yl)-aniline, imidazole, and 4-imidazoleacrylic acid,
    wherein the pH-sensitive carbon nanoparticles encapsulate the drug by hydrophobic interaction between the hydrophobic drug and the pH-sensitive carbon nanoparticles,
    wherein the pH-sensitive carbon nanoparticles have a neutral charge or positive charge at pH to release the drug.

2. The drug carrier of claim 1, wherein the drug is at least one selected from the group consisting of a chlorine-based drug and a porphyrin-based drug.

3. The drug carrier of claim 1, wherein the drug is at least one anticancer agent selected from the group consisting of doxorubicin, paclitaxel, cisplatin, sirolimus and etoposide, or at least one photosensitizer selected from the group consisting of chlorine e6, pheophorbide a and phthalocyanine.

4. The drug carrier of claim 1, wherein the drug carrier is destabilized at a pH of 7.0 or less.

5. The drug carrier of claim 1, wherein the drug carrier is used for cancer treatment, photodynamic therapy or photomediated anti-cancer immunotherapy.

6. A method of preparing a drug carrier comprising pH-sensitive carbon nanoparticles and a hydrophobic drug, comprising:
    preparing pH-sensitive carbon nanoparticles, comprising:
        preparing citric acid solution by dissolving citric acid;
        preparing a mixed solution by adding an imidazole compound to the citric acid solution, wherein the imidazole compound is at least one selected from the group consisting of 1-(3-aminopropyl) imidazole, 4-imidazoleacetic acid hydrochloride, 4-(1H-imidazole-1-yl)-aniline, imidazole, and 4-imidazoleacrylic acid;
        preparing carbon nanoparticles by heat-treating the mixed solution comprising microwave assistant pyrolysis, hydrothermal reaction, and an autoclave reaction for the mixed solution; and
        dialysis and freeze-drying the carbon nanoparticles; and
    encapsulating the hydrophobic drug with the pH-sensitive carbon nanoparticles under alkaline condition, by hydrophobic interaction between the hydrophobic drug and the pH-sensitive carbon nanoparticles,
    wherein the pH-sensitive carbon nanoparticles have a neutral charge or positive charge at pH to release the drug.

7. The method of claim 6, wherein the microwave pyrolysis reaction is performed for 1 to 5 minutes in a microwave.

8. The method of claim 6, wherein the hydrothermal reaction is performed for 4 to 8 hours in an oil bath at 100 to 200° C.

9. The method of claim 6, wherein the autoclave reaction is performed for 8 to 12 hours in an autoclave at 100 to 150° C.

* * * * *